(12) United States Patent
Ramsey

(10) Patent No.: US 6,342,142 B1
(45) Date of Patent: *Jan. 29, 2002

(54) APPARATUS AND METHOD FOR PERFORMING MICROFLUIDIC MANIPULATIONS FOR CHEMICAL ANALYSIS

(75) Inventor: J. Michael Ramsey, Knoxville, TN (US)

(73) Assignee: UT-Battelle, LLC, Oak Ridge, TN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/300,060

(22) Filed: Apr. 27, 1999

Related U.S. Application Data

(63) Continuation of application No. 08/283,769, filed on Aug. 1, 1994, now Pat. No. 6,001,229.

(51) Int. Cl.[7] ............... G01N 27/26; G01N 27/447; B01D 57/02
(52) U.S. Cl. ............... 204/453; 204/450; 204/451; 204/600; 204/601; 204/604; 422/100
(58) Field of Search ............... 204/450, 451, 204/452, 453, 454, 455, 600, 601, 602, 603, 604, 605; 422/100

(56) References Cited

U.S. PATENT DOCUMENTS

| | | | | |
|---|---|---|---|---|
| 4,390,403 A | * | 6/1983 | Batchlder | 204/547 |
| 5,126,022 A | * | 6/1992 | Soane et al. | 204/458 |
| 5,207,880 A | * | 5/1993 | Middendorf et al. | 204/461 |
| 5,229,297 A | | 7/1993 | Schnipelsky et al. | 436/94 |
| 5,230,781 A | * | 7/1993 | Middendorf et al. | 204/612 X |
| 5,288,463 A | | 2/1994 | Chemelli | 422/58 |
| 5,307,148 A | * | 4/1994 | Kambara et al. | 204/481 X |
| 5,338,427 A | * | 8/1994 | Shartle et al. | 204/604 |
| 5,376,252 A | * | 12/1994 | Ekstrom et al. | 204/604 |
| 5,429,734 A | | 7/1995 | Gajar et al. | 204/603 |
| 5,543,026 A | * | 8/1996 | Hoff et al. | 204/612 |

OTHER PUBLICATIONS

Andreas Manz et al, "Capillary Electrophoresis on a chip" Journal of Chromatography, vol. 593, pp. 253–258, 1992.*

(List continued on next page.)

*Primary Examiner*—Jill Warden
*Assistant Examiner*—John S. Starsiak, Jr.
(74) *Attorney, Agent, or Firm*—Dann Dorfman Herrell and Skillman, P. C.

(57) ABSTRACT

A microchip apparatus and method provide fluidic manipulations for a variety of applications, including sample injection for microchip liquid chromatography. The microchip is fabricated using standard photolitographic procedures and chemical wet etching, with the substrate and cover plate joined using direct bonding. Capillary electrophoresis is performed in channels formed in the substrate. Injections are made by electro-osmotically pumping sample through the injection channel that crosses the separation channel, followed by a switching of the potentials to force a plug into the separation channel.

59 Claims, 15 Drawing Sheets-

OTHER PUBLICATIONS

D.J. Harrison et al, "Miniaturized Chemical Analysis Systems and their Fabrication: An Alternative of Chemical Sensors" The Electro Chemical Society, Inc. pp. 546–553, May 1993.*

D.N. Harrison et al, "Integrated Electrophoresis Systems for Bio–Chemical Analyses" Solid–State Sensor and Actuator Workshop, Jun. 1994.*

Stephen C. Jacobson et al, "Effects of Injection Schemes and Column Geometry on the Performances of Microchip Electrophoresis Devices" Analytical Chemistry, vol. 66, No. 7 (Apr. 1, 1994) 1107–1113, Apr. 1, 1994.*

M. Deml, F. Foret, and P. Boček, "Electric Sample Splitter for Capillary Electrophoresis" Journal of Chromatography, 320 (1985) 159–165.*

D. Jed Harrison, Andreas Manz, Zhonghu, Fan, Hans Lüdi, and H. Michael Widmer, Capillary Electrophoresis and Sample Injection Systems.*

Integrated on a Planar Glass Chip Analytical Chemistry, vol. 64, No. 17 (Sep. 1, 1992) 1926–1932.*

D. Jed Harrison, Karl Fluri, Kurt Seiler, Zhonghu, Fan, Carlo S. Effenhauser, Andreas Manz, "Micromachining a Minaturized Capillary Electrophoresis Based Chemical Analysis System in a Chip" Science, vol. 261, (Aug. 13, 1993) 895–897.*

Carlo S. Effenhauser, Andreas Manz, and H. Michael Widmer, "Glass Chips for High Speed Capillary Electrophoresis Separations with Submicrometer Plate Heights" Analytical Chemistry, vol. 65, No. 19 (Oct. 1, 1993) 2637–2642.*

Stephen C. Jacobson et al, "Effects of Injection Schemes and Column Geometry on the Performance of Microchip Electrophoresis Devices". Analytical Chemistry, vol. 66, No. 7 (Apr. 1, 1994).*

D.J. Harrison et al., "Miniaturized Chemical Analysis Systems and their Fabrication: An Alternative to Chemical Sensors", The Electrochemical Society, Inc., 546–553.

D. Jed Harrison et al., Transducers '91—Digest of Technical Papers—IIII, pp. 792–795.

R. Miyake et al., MEMS, IEEE, 248–253 (1993).

N. Burggraf et al., Sensors and Actuators, B20, 103–110 (1994).

N. Burggraf et al., Journal of High Resolution Chromatography, 16: 594–596 (1993).

N. Burggraf et al., Analytical Methods and Instrumentation, 1: 55–59 (1993).

C.S. Effenhauser et al., Analytical Chemistry, 66: 2949–2953 (1994).

K. Seiler et al., Analytical Chemistry, 66: 3485–3491 (1994).

$17^{th}$ International Symposium on Column Liquid Chromatography (May 9–14, 1993) (Abstract).

Abstract and miscellaneous slides (Date unknown).

Jacobson et al., Electrically Driven Separations on a Microchip, Sensor and Actuator Workshop, Hilton Head, SC (Jun. 13–16, 1994).

Jacobsen et al., Open Channel Electrochromatography on a Microchip, 66 Anal. Chem., 2369–2373 (1994).

Harrison et al., Towards Miniaturized Electrophoresis and Chemical Analysis Systems on Silicon: An Alternative to Chemica Sensors, Sensors and Actuators B, 10: 107–116 (1993).

Manz et al., Planar Chips Technology for Miniaturization and Integration of Separation Techniques into Monitoring Systems: Capillary Electrophoresis on a Chip, J. Chromatography, 593: 253 (1992).

Harrison et al., Integrated Electrophoresis Systems for Biochemical Analyses, Solid State Sensor and Actuator Workshop (Conf. Proc. pp. 21–24).

* cited by examiner

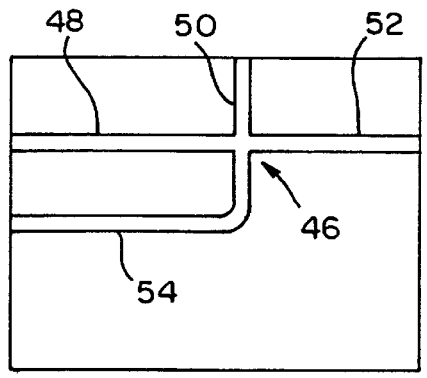
FIG. 3a
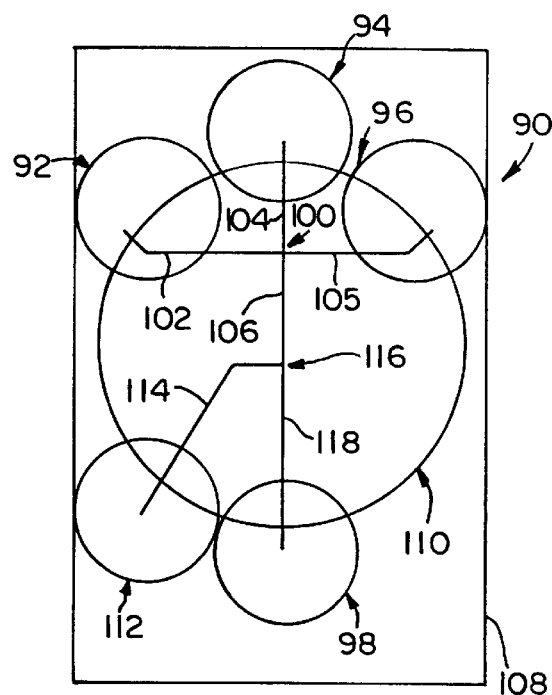
FIG. 16
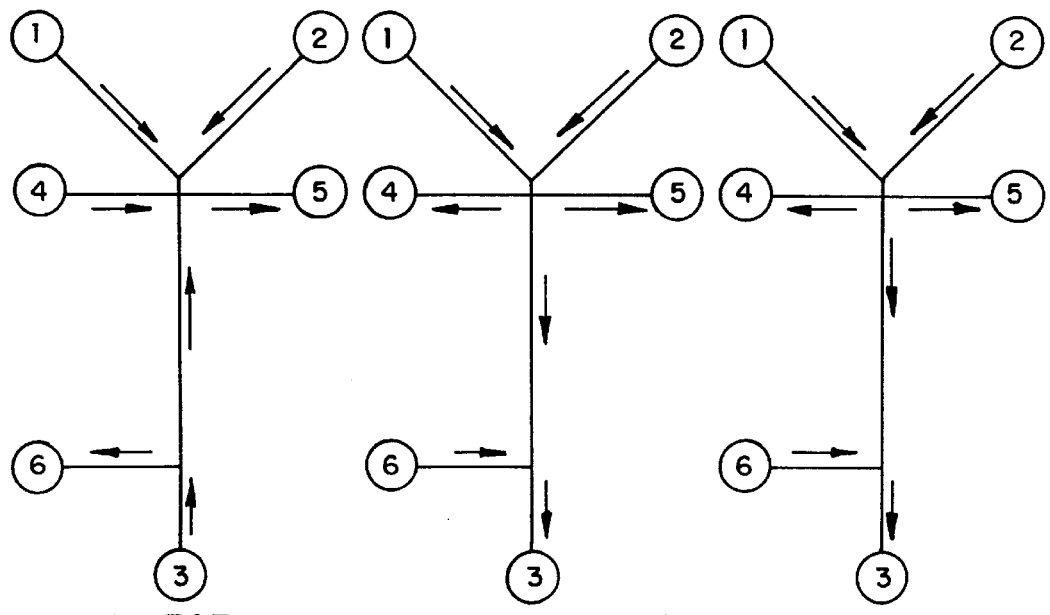
INJECT
FIG.21a
RUN (START)
FIG.21b
RUN (FINISH)
FIG.21c

APPARATUS AND METHOD FOR PERFORMING MICROFLUIDIC MANIPULATIONS FOR CHEMICAL ANALYSIS

This application is a continuation of U.S. patent application No. 08/283,769, filed Aug. 1, 1994, now U.S. Pat. No. 6,001,229.

This invention was made with Government support under contract DE-AC05-840R21400 awarded by the U.S. Department of Energy to Martin Marietta Energy Systems, Inc. and the Government has certain rights in this invention.

FIELD OF THE INVENTION

The present invention relates generally to miniature instrumentation for chemical analysis and chemical sensing and, more specifically, to electrically controlled manipulations of fluids and capillaries in micromachine channels. These manipulations can be used in a variety of applications, including the electrically controlled manipulation of fluid for capillary electrophoresis, liquid chromatography, and flow injection analysis.

BACKGROUND OF THE INVENTION

Capillary electrophoresis has become a popular technique for separating charged molecular species in solution. The technique is performed in small capillary tubes to reduce band broadening effects due to thermal convection and hence improve resolving power.

The small tubes imply that minute volumes of materials, on the order of picoliters, must be handled to inject the sample into the separation capillary tube.

Current techniques for injection include electromigration and siphoning of sample from a container into a continuous separation tube. Both of these techniques suffer from relatively poor reproducibility, and electromigration additionally suffers from electrophoretic mobility-based bias. For both sampling techniques the input end of the analysis capillary tube must be transferred from a buffer reservoir to a reservoir holding the sample. Thus, a mechanical manipulation is involved. For the siphoning injection, the sample reservoir is raised above the buffer reservoir holding the exit end of the capillary for a fixed length of time.

An electromigration injection is effected by applying an appropriately polarized electric potential across the capillary tube for a given duration while the entrance end of the capillary is in the sample reservoir. This can lead to sampling bias because a disproportionately larger quantity of the species with higher electrophoretic mobilities migrate into the tube. The capillary is removed from the sample reservoir and replaced into the entrance buffer reservoir after the injection duration for both techniques.

U.S. Pat. No. 4,908,112 to Pace describes a micromachined structure that includes a channel for the separation and a separate channel that meets the separation channel in a T-intersection and contains electrodes to produce electroosmotic flow for injection of sample into the separation channel.

U.S. Pat. No. 5,141,621 to Zare et al. discloses a capillary electrophoresis method and apparatus which applies a potential at two buffer reservoirs located at opposite ends of a capillary column. Samples are introduced without the need to disengage the electyric field, due to the fact that the injector is grounded.

U.S. Pat. No. 5,110,431 to Moring describes a crossing flow pattern using conventional capillary tubing with minimal resolution loss for the purpose of post column introduction of reactive substances to aid in detection.

U.S. Pat. No. 5,092,973 to Zare et al. describes a capillary with rectangular geometry, which certain specified advantages in a capillary electrophoresis technique.

U.S. Pat. No. 5,073,239 to Hjerten discloses the use of two capillaries to deliver sample by electroendosmotic flow into a closed container whose major exit is through the separating column.

A continuing need exists for methods and apparatuses which lead to improved electrophoretic resolution and improved injection stability.

SUMMARY OF THE INVENTION

An object of the present invention is to provide a miniaturized injection method and apparatus in which it is not required to perform any mechanical manipulations with the capillary tube.

Another object of the present invention is to provide a miniaturized injection method and apparatus which utilizes electroosmottic pumping similar to electromigration techniques, but without the advent of sampling bias.

Yet another object of the present invention is to provide a miniaturized injection method and apparatus capable of achieving improvements in reproducibility of injections.

Still another object of the present invention is to provide a miniaturized injection method and apparatus which uses electrostatic forces to spatially shape the injection plug, making it small in spatial extent and stable with time.

Another object of the invention is to provide a reagent mixing apparatus and method for electroosmotically driven devices which allow virtually any wet chemical experiment now performed at the bench, in test tubes and beakers, to be conducted on a chip under electronic control.

These and other objects of the invention are met by providing a method of controlling fluid flow in an inter-conncected channel structure having at least three ports, which includes actively controlling the electric potential at the at least three ports to create diffferences in potential sufficient to cause fluid to move through the interconnected channel structure in a controlled manner. The aforementioned objects are further met by providing an apparatus for effecting the method.

In another aspect of the invention, an injection apparatus is provided for microchip liquid chromatography and other situations, which includes a body having a first channel extending between an analyte reservoir and an analyte waste reservoir and a second channel extending between a first buffer reservoir and a buffer waste reservoir, the first and second channels crossing to form a first fluid communicating intersection, and means for moving analyte, in sequence, and at first, through the first channel into the intersection, and then from the intersection into the second channel.

Other objects, advantages and salient features of the invention will become apparent from the following detailed description, which taken in conjunction with the annexed drawings, discloses preferred embodiments of the invention.

BRIEF DESCRIPTION OF THE DRAWINGS

FIG. 3(a) is a schematic view of the intersection area of the microchip of FIG. 1, prior to analyte injection;

FIG. 16 is a schematic, top plan view of a microchip according to the FIG. 14 embodiment, additionally including a reagent reservoir and reaction channel;

FIG. 21 is a schematic view of the apparatus of FIG. 20, showing sequential applications of voltages to effect desired fluidic manipulations.

DETAILED DESCRIPTION OF THE INVENTION

Figure 1:
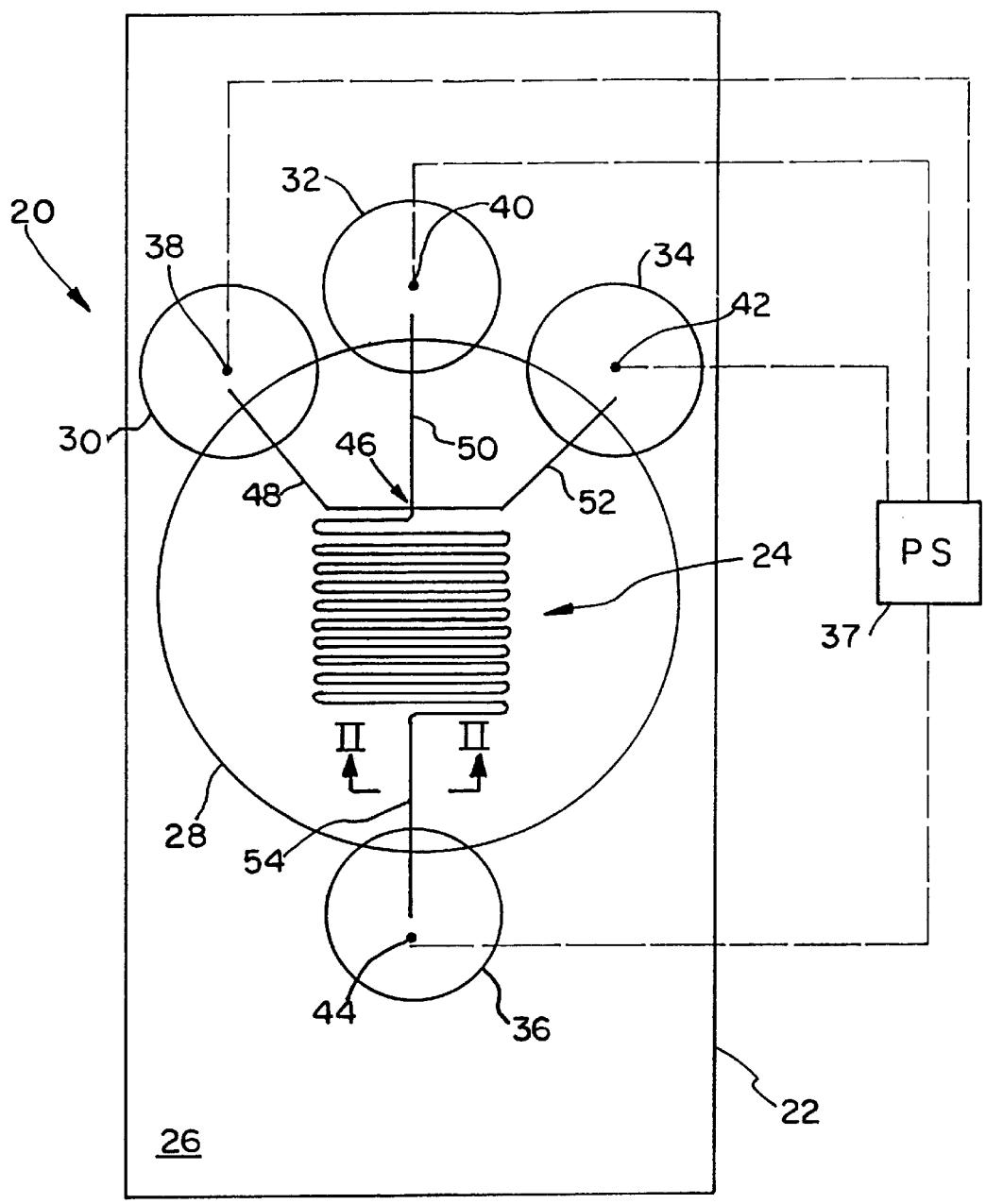
FIG. 1 is a schematic top view of a microchip according to a first preferred embodiment of a microchip according to the present invention.

Referring to FIG. 1, a microchip 20 includes a base member 22 which is approximately two inches by one inch piece of microscope slide (Corning, Inc. #2947). A channel pattern 24 is formed in one planar surface 26 of the base member 22 using standard photolitographic procedures followed by chemical wet etching.

The channel pattern 24 is transferred onto the slide or base member 22 with a positive photoresist (Shipley 1811) and an e-beam written chrome mask (Institute of Advanced Manufacturing Sciences, Inc.). The pattern is chemically etched using $HF/NH_4F$ solution.

After forming the channel pattern 24, a cover plate 28 is then bonded to the base member 22 using a direct bonding technique whereby the base member 22 and the cover plate 28 surfaces are first hydrolyzed in a dilute $NH_4OH/H_2O_2$ solution and then joined. The assembly is then annealed at about 500° C. in order to insure proper adhesion of the cover plate 28 to the base member 22.

Following bonding of the cover plate 28, cylindrical plastic reservoirs 30, 32, 34 and 36, having open opposite axial ends, are affixed to the base member 22, with portions of the cover plate sandwiched therebetween, with epoxy or other suitable means. Electrical contact is made by placing platinum electrodes 38, 40, 42, and 44 in reservoirs 30, 32, 34, and 36, respectively. The electrodes are connected to a power source (PS) 37 which applies a desired potential to select ones of the electrodes, in a manner to be described more fully below.

The channel pattern 24 has four distinct channel portions. Each channel portion has an accompanying reservoir mounted above the terminus of each channel portion, and all four intersect at one end in a four way intersection 46. The opposite ends of each section provide termini that extend just beyond the peripheral edge of the cover plate 28.

A first channel portion 48 runs from the reservoir 30 to the four-way intersection 46. A second channel portion 50 runs from the reservoir 32 to the four-way intersection 46. A third channel portion 52 runs from the reservoir 34 to the intersection 46, and a fourth channel portion 54 runs from the reservoir 44 to the intersection 46.

In one particularly preferred embodiment, the enclosed length (that which is covered by the cover plate 28 ) of channel extending from reservoir 30 to reservoir 34 is 19 mm, while the length of channel portion 50 is 6.4 mm and channel portion 54 is 171 mm. The turn radius of section 54, which serves as a separation column, is 0.16 mm.

Figure 2:
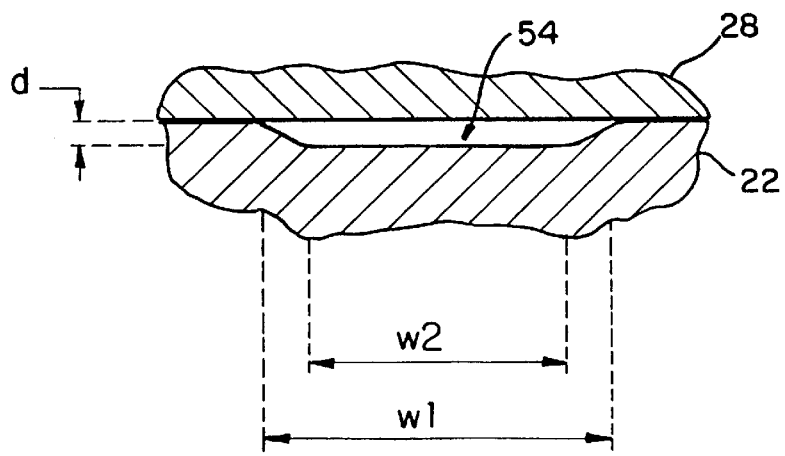
FIG. 2 is an enlarged, vertical sectional view of a channel, taken along line II—II of FIG. 1.

The cross section of the channel 54 is shown in FIG. 2. The other channels would have the same shape. The dimensions give the channel 54 a trapezoidal shape. In one specific application, the channel 54 has a depth "d" of 10 $\mu$m, an upper width "w1" of 90 $\mu$m, and a lower width "w2" of 70 $\mu$m. The trapezoidal cross section is due to "undercutting" by the chemical etching process at the edge of the photoresist.

Electrophoresis experiments were conducted using the microchip 20 of FIG. 1, and employing methodology according to the present invention. Chip dynamics were analyzed using analyte fluorescence. A charge coupled device (CCD) camera was used to monitor designated areas of the chip and a photomultiplier tube (PMT) tracked single point events. The CCD (Princeton Instruments, Inc. TE/CCD-512 TKM) camera was mounted on a stereo microscope (Nikon SMZ-U), and the chip 20 was illuminated using an argon ion laser (514.5 nm, Coherent Innova 90) operating at 3 W with the beam expanded to a circular spot ≈2 cm in diameter. The point detection scheme employed a helium-neon laser (543 nm, PMS Electro-optics LHGP-0051) with an electrometer (Keithley 617) to monitor response of the PMT (Oriel 77340). The power supply or supplies 37 (Spellman CZE 1000R) for electrophoresis were operated between 0 and +4.4 kV relative to ground.

General Operation

Referring again to FIG. 1, the chip 20 can be operated in either an "inject" mode or a "run" mode. Reservoir 30 is supplied with an analyte and reservoir 32 with buffer. Reservoir 34 acts as an analyte waste reservoir, and reservoir 36 acts as a waste reservoir.

In the inject mode, at least two types of sample introduction are possible. In the first, known as a "floating" injection, a potential is applied to reservoir 30 with reservoir 34 grounded. At the same time, reservoirs 32 and 36 are floating, meaning that they are neither coupled to the power source, nor grounded.

The second inject mode is the "pinched" mode, which is preferred, wherein potentials are applied to reservoirs 30, 32, and 36, with reservoir 34 grounded in order to control the injection plug shape.

In the "run" mode, the potential is applied to reservoir 32 with reservoir 36 grounded and with reservoirs 30 and 34 at approximately half of the potential of reservoir 32.

The analytes used for diagnostic experiments were rhodamine B and sulforhodamine 101 (Exciton Chemical Co., Inc.) at 60 μM for the CCD images and 6 μM for the point detection. A sodium tetraborate buffer (50 mM, pH 9.2) was the mobile phase in all experiments.

The two modes of injection were tested for the sample introduction into the separation column, channel portion 54. The analyte was placed in reservoir 30, and in both injection schemes is "pumped" in the direction of reservoir 34, a waste reservoir. CCD images of the two types of injections are depicted in FIGS. 3(a)–3 (c). FIG. 3(a) shows the intersection 46, as well as the end portions of channel portions 48, 50, 52 and 54.

Figure 3B:
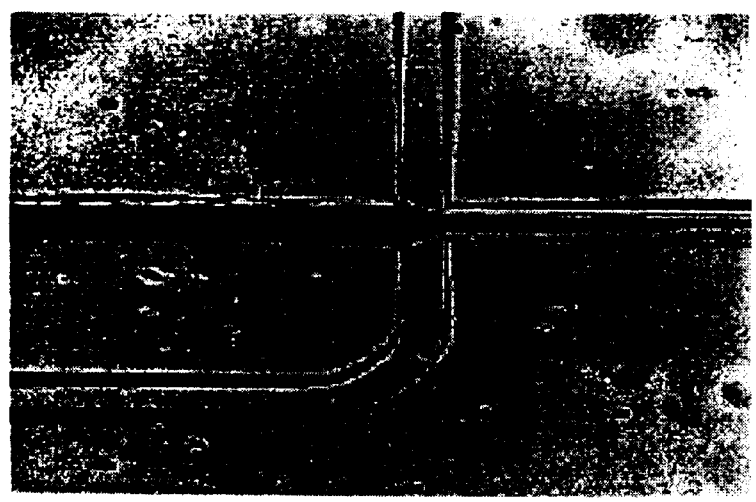
FIG. 3(b) is an actual CCD fluorescence image taken of the same area depicted in FIG. 3(a), after injection in the pinched mode.

The CCD image of FIG. 3(b) is of injection in the pinched mode, just prior to being switched to the run mode. In the pinched mode, analyte (shown as white against the dark background) is pumped electrophoretically and electroosmotically from reservoir 30 to 34 (left to right) with mobile phase from reservoir 32 (top) and reservoir 36 (bottom) travelling toward reservoir 34 (right). The voltages applied to reservoirs 30, 32, 34, and 36 were 90%, 90%, 0, and 100%, respectively, of the power supply output which correspond to electric field strengths in the corresponding channels of 270, 400, 690 and 20 V/cm, respectively. Consequently, the analyte in the injection cross or intersection 46 has a trapezoidal shape and is spatially constricted in channel portion 52 by this flow pattern.

Figure 3C:
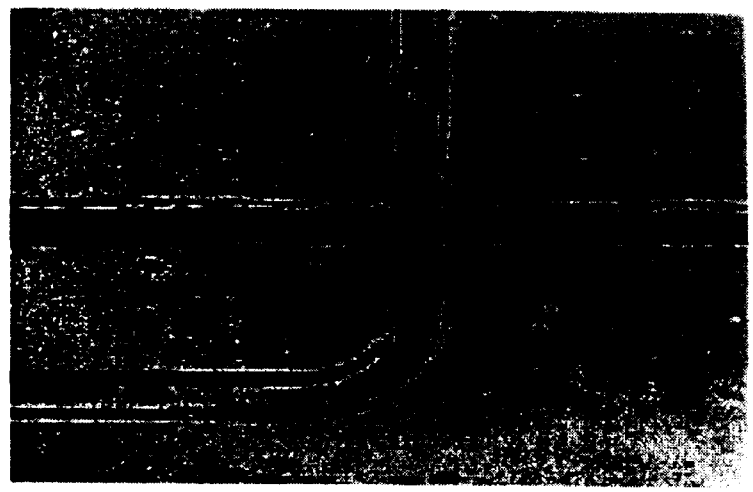
FIG. 3(c) is an actual photomicrograph taken of the same area depicted in FIG. 3(a), after injection in the floating mode.

FIG. 3(c) shows a floating mode injection. The analyte is pumped from reservoir 30 to 34 as in the pinched injection except no potential is applied to reservoirs 32 and 36. By not controlling the flow of mobile phase in channel portions 50 and 54, the analyte is free to flow into these channels through eddy flow resulting in a more diffuse injection plug.

When comparing the pinched and floating injections, the pinched injection is superior in two areas: temporal stability and plug length. When two or more analytes with vastly different mobilities are to be analyzed, an injection with temporal stability insures that equal volumes of the faster and slower moving analytes are introduced into the separation column or channel 54. A smaller plug length leads to a higher separation efficiency and, consequently, to a greater component capacity for a given instrument.

Figure 4:
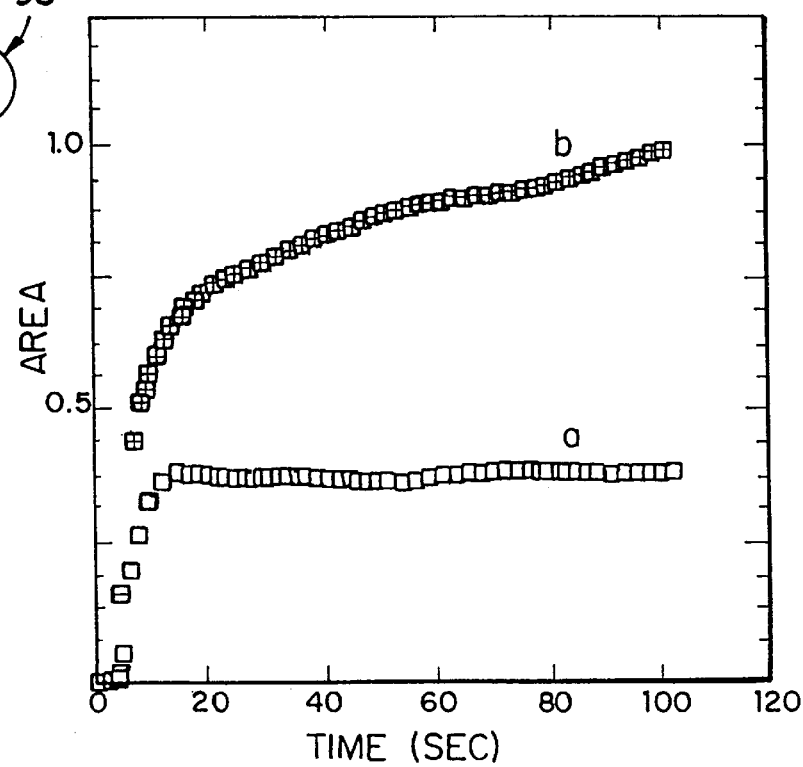
FIG. 4 shows integrated fluorescence plotted versus time for pinched and floating injections.

To determine the temporal stability of each mode, a series of CCD fluorescent images were collected at 1.5 second intervals starting just prior to the analyte reaching the injection intersection 46. An estimate of the amount of analyte that is injected was determined by integrating the fluorescence in the intersection 46 and channels 50 and 54. This fluorescence is plotted versus time in FIG. 4.

For the pinched injection, a stability of 1% relative standard deviation (RSD) is observed, which is comparable to the stability of the illuminating laser. For the floating injection, the amount of analyte to be injected into the column or channel portion 54 increases with time because of the flow anisotropy. For a 30 second injection, the volume of the injection plug is ca. 90 pL and stable for the pinched injection versus ca. 300 pL and continuously increasing with time for a floating injection.

By monitoring the separation channel at a point 0.9 cm from the intersection 46, the reproducibility for the pinched injection mode was tested by integrating the area of the band profile following introduction into the separation channel 54. For six injections with a duration of 40 seconds, the reproducibility for the pinched injection is 0.7% RSD. Most of this measured instability is from the optical measurement system. The pinched injection has a higher reproducibility because of the temporal stability. With electronically controlled voltage switching, the RSD is expected to improve for both schemes.

The injection plug width and, ultimately, the resolution between analytes depends largely on both the flow pattern of the analyte and the dimensions of the injection cross or intersection 46. For this column, the width of the channel at the top is 90 μm, but a channel width of 10 μm is feasible which would lead to a decrease in the volume of the injection plug from 90 pL down to 1 pL with a pinched injection.

Separations

Figure 5A:
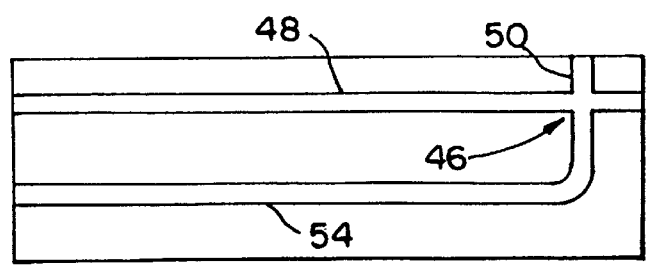
FIG. 5(a) is a schematic view of a CCD camera view of the intersection area of the microchip of FIG. 1, prior to analyte injection.

After the sample or analyte has been pumped into the intersection 46 of the microchip 20, the voltages are manually switched from the inject to the run mode of operation. FIGS. 5(a)–5 (e) illustrate a separation of rhodamine B (less retained) and sulforhodamine (more retained) using the following conditions: $E_{inj}$=400 V/cm, $E_{run}$=150 V/cm, buffer=50 nM sodium tetraborate at pH 9.2. The CCD images demonstrate the separation process at 1 second intervals, with FIG. 5(a) showing a schematic of the section of the chip imaged, and with FIGS. 5(b)–5 (e) showing the separation unfold.

Figure 5B:
FIG. 5(b) is a CCD fluorescence image taken of the same area depicted in FIG. 5(a), after injection in the pinched mode.
Figure 5C:
FIGS. 5(c)–5(e) are CCD fluorescence images taken of the same area depicted in FIG. 3(a), sequentially showing a plug of analyte moving away from the channel intersection at 1, 2, and 3 seconds, respectively, after switching to the run mode.

FIG. 5(b) again shows the pinched injection with the applied voltages at reservoirs 30, 32, and 36 equal. FIGS. 5(c)–5 (e) shows the plug moving away from the intersection at 1, 2, and 3 seconds, respectively, after switching to the run mode.

In FIG. 5(c), the injection plug is migrating around a 90° turn, and band distortion is visible due to the inner portion of the plug travelling less distance than the outer portion. By FIG. 5(d), the analytes have separated into distinct bands, which are distorted in the shape of a parallelogram. In FIG. 5(e), the bands are well separated and have attained a more rectangular shape, i.e., collapsing of the parallelogram, due to radial diffusion, an additional contribution to efficiency loss.

When the switch is made from the inject mode to the run mode, a clean break of the injection plug from the analyte stream is mandatory to avoid tailing. This is achieved by pumping the mobile phase from channel 50 into channels 48, 52, and 54 simultaneously by maintaining the potential at the intersection 46 below the potential of reservoir 32 and above the potentials of reservoirs 30, 34, and 36.

The experiments described herein, the intersection 46 was maintained at 66% of the potential of reservoir 32 during the run mode. This provided sufficient flow of the analyte back away from the injection intersection 46 down channels 48 and 52 without decreasing the field strength in the separation channel 54 significantly.

Figure 5D:
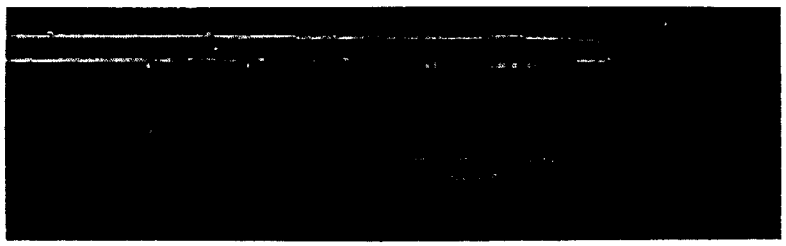
Figure 5E:
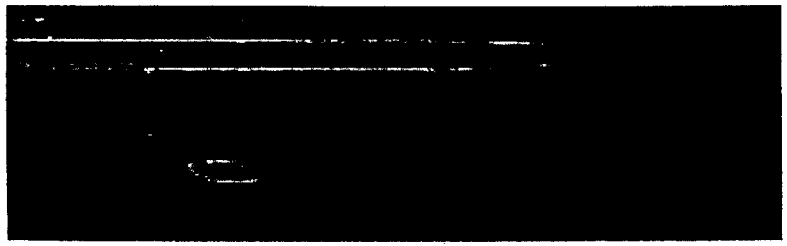

This three way flow is demonstrated in FIGS. 5(c)–5(e) as the analytes in channels 48 and 52 (left and right, respectively) move further away from the intersection with time. Three way flow permits well-defined, reproducible injections with minimal bleed of the analyte into the separation channel 54.

Figure 6:
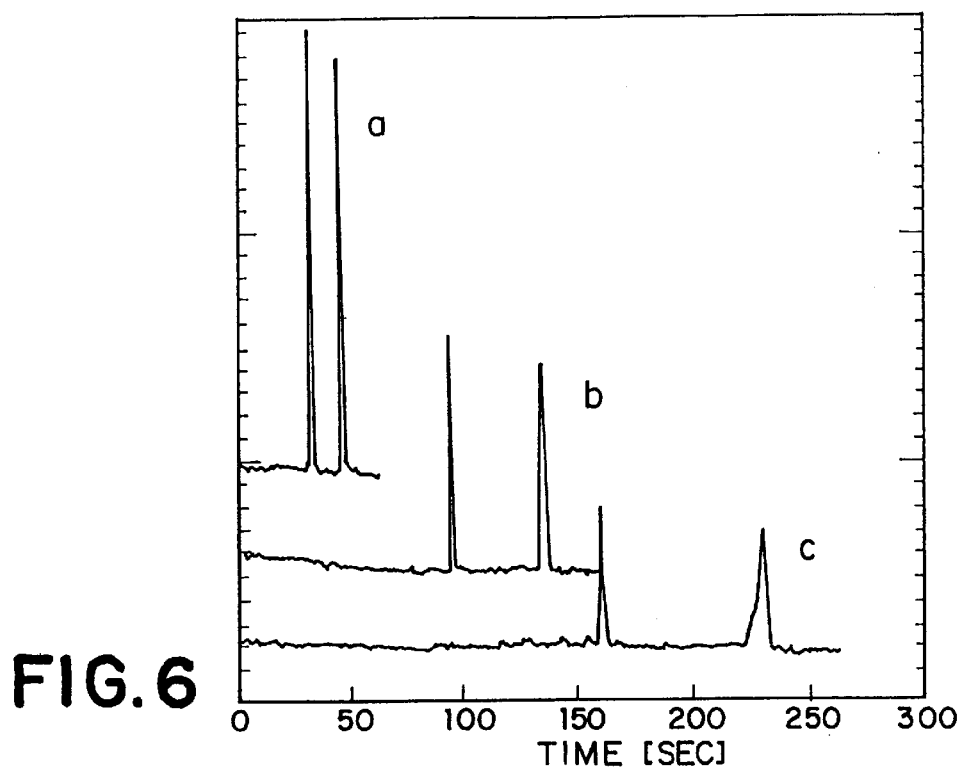
FIG. 6 are electropherograms at (a) 3.3 cm, (b) 9.9 cm, and (c) 16.5 cm from the point of injection for rhodamine B (less retained) and sulforhodamine (more retained)

FIG. 6 are electropherograms at (a) 3.3 cm, (b) 9.9 cm, and (c) 16.5 cm from the point of injection for rhodamine B (less retained) and sulforhodamine (more retained). These were taken using the following conditions: injection type was pinched, $E_{inj}$=500V/cm, $E_{run}$=170 V/cm, buffer=50 mM sodium tetraborate at pH 9.2.

Figure 7:
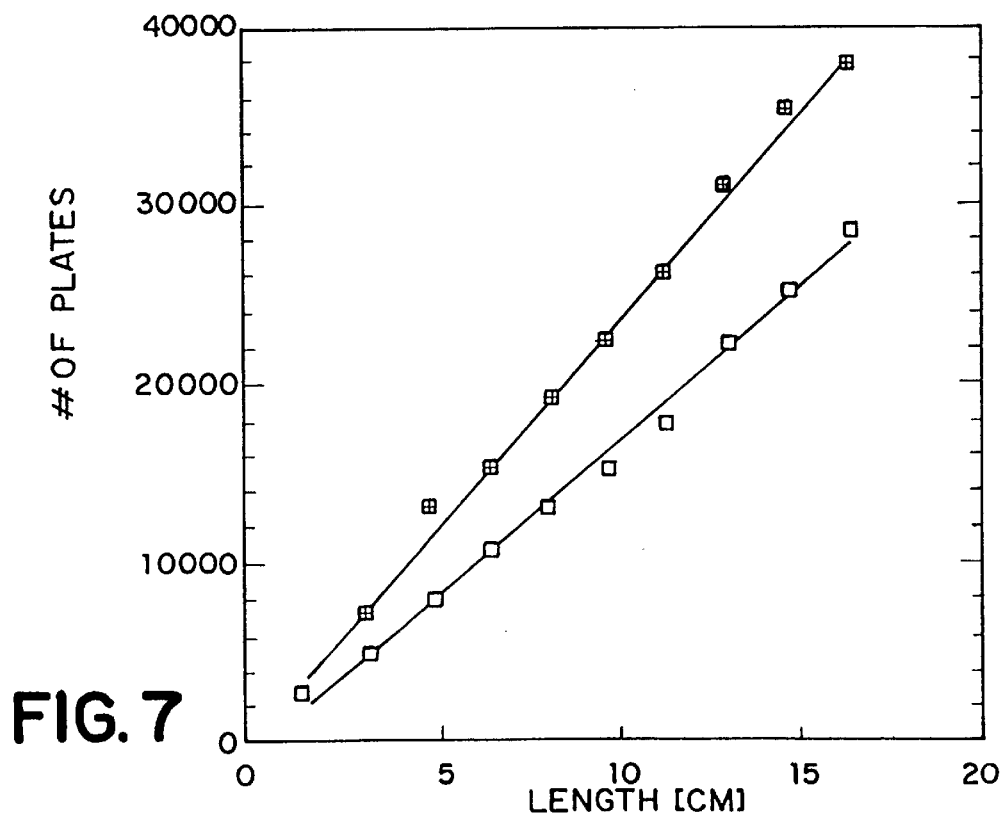
FIG. 7 is a plot of the efficiency data generated from the electropherograms of FIG. 6, showing variation of the plate number with channel length for rhodamine B (square with plus) and sulforhodamine (square with dot) with best linear fit (solid lines) for each analyte.

To obtain electropherograms in the conventional manner, single point detection with the helium-neon laser was used at different locations down the axis of the separation channel 54. The efficiency at ten evenly spaced positions was monitored, each constituting a separate experiment. FIG. 6 depicts selected electropherograms at 3.3, 9.9, and 16.5 cm from the point of injection. The efficiency data are plotted in FIG. 7 (conditions for FIG. 7 were the same as for FIG. 6).

At 16.5 cm from the point of injection, the efficiencies of rhodamine B and sulforhodamine are 38,100 and 29,000 plates, respectively. Efficiencies of this magnitude are sufficient for many separation applications. The linearity of the data provides information about the uniformity and quality of the channel down the length of the column. If a defect in the channel, e.g. a large pit, was present, a sharp decrease in the efficiency would result; however, none was detected.

Figure 8:
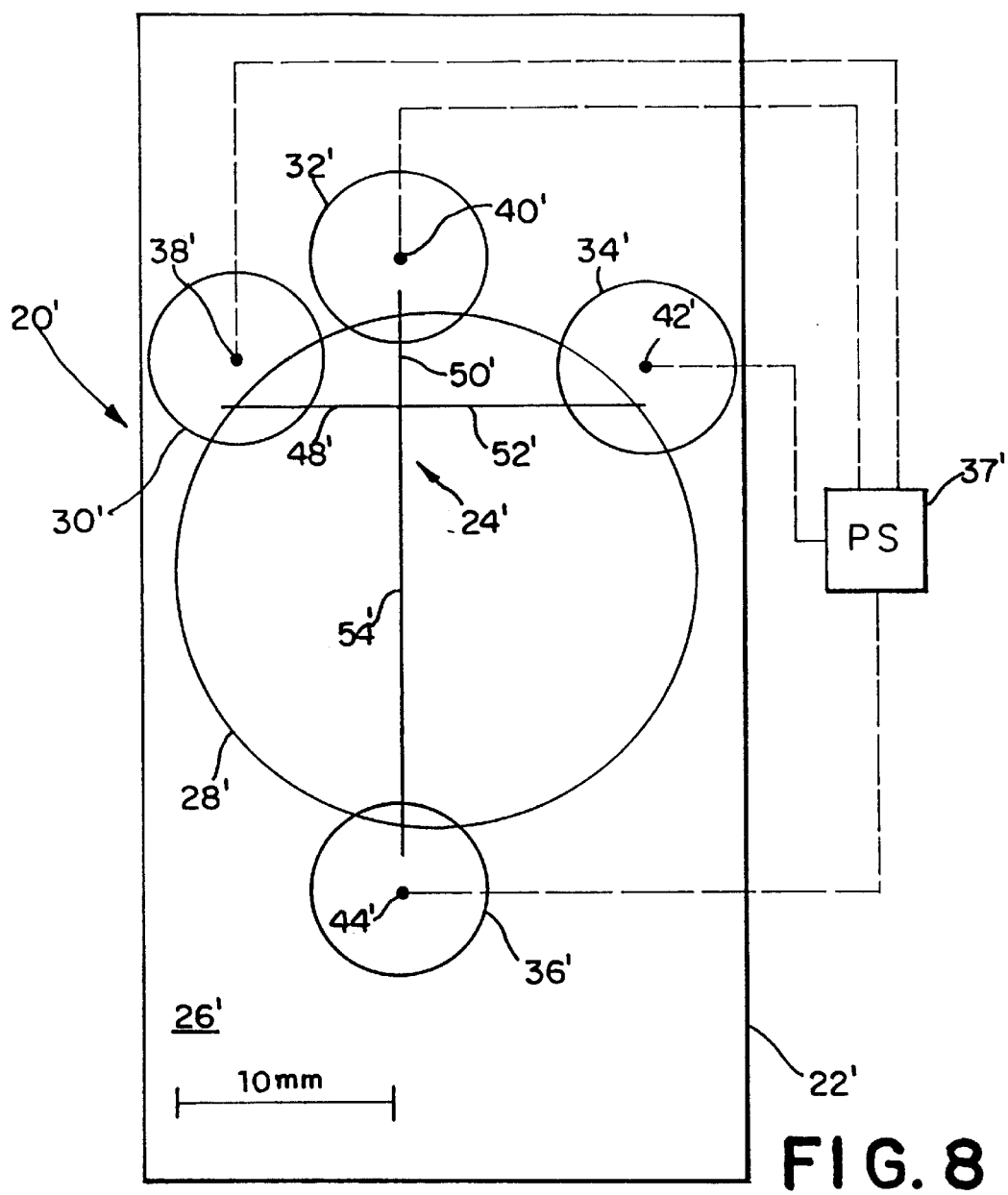
FIG. 8 is a schematic top view of a microchip according to a second preferred embodiment of a microchip according to the present invention.

As a further demonstration of the utility of this injection scheme, a modified embodiment was tested. Referring to FIG. 8, the same, but primed, reference numerals are used to refer to structure similar to that found in FIG. 1. a The only significant difference is that instead of a serpentine channel 54 for separations, a straight channel 54' is used. A variety of tests, according to the aforementioned techniques, were performed, but with higher electric field strengths used over shorter distances to achieve high speed separations. A spatially well defined small volume, ≈100 pL, injection is required to perform these types of analyses.

Figure 9:
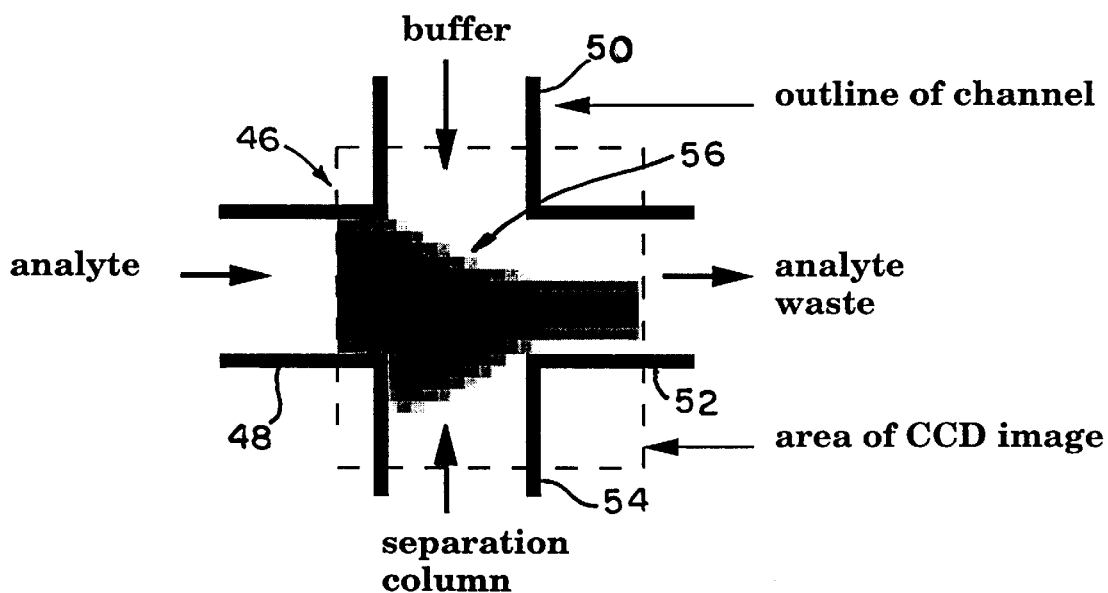
FIG. 9 is a CCD image of "sample loading mode for rhodamine B (shaded area)

The sample was loaded into the injection cross via a frontal electropherogram, and once the front of the slowest analyte passes through the injection cross or intersection 46', the sample is ready to be analyzed. In FIG. 9, a CCD image (the area of which is denoted by the broken line square) displays the flow pattern of the analyte 56 (shaded area) and the buffer (white area) through the region of the injection intersection 46.

By pinching the flow of the analyte, the volume of the analyte plug is stable over time. The slight asymmetry of the plug shape is due to the different electric field strengths in the buffer channel 50 (470 V/cm) and the separation channel 54 (100 V/cm), for 1.0 kV applied to the buffer, the analyte and the waste reservoirs, and with the analyte waste reservoir grounded. However, the different field strengths do not influence the stability of the injection plug. Ideally, when the analyte plug is injected into the separation column, only the analyte in the injection cross or intersection 46 would migrate into the separation channel 54.

From FIG. 9, the volume of the injection plug in the injection cross is approximately 120 pL with a plug length of 130 μm. A portion of the analyte in the analyte channel and the analyte waste channel is drawn into the separation column. Following the switch to the separation mode, the volume of the injection plug is approximately 250 pL with a plug length of 208 μm. These dimensions are estimated from a series of CCD images taken immediately after the switch is made to the separation mode.

Figure 10A:
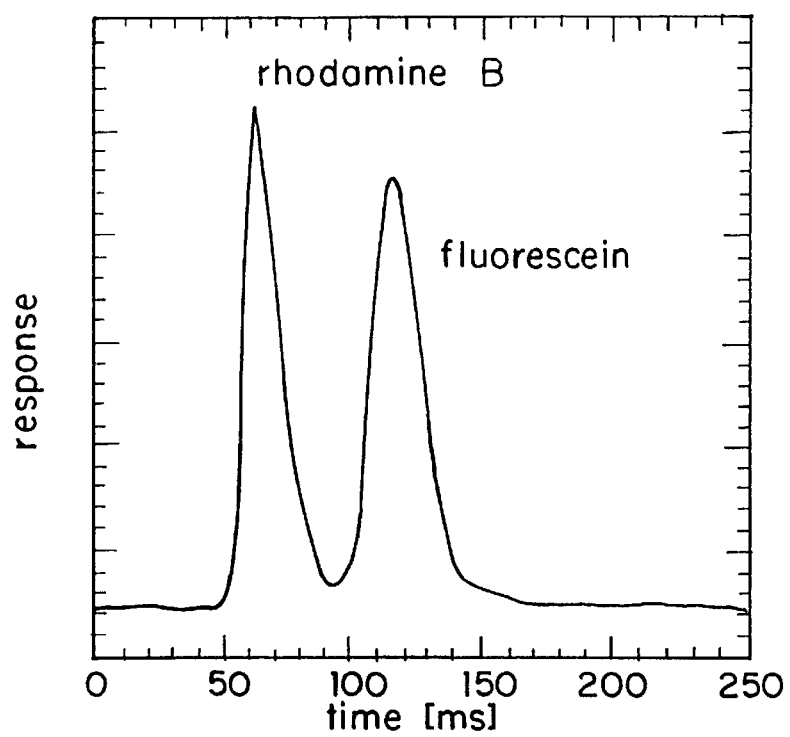
FIG. 10(a) is an electropherogram of rhodamine B and fluorescein with a separation field strength of 1.5 kV/cm and a separation length of 0.9 mm.
Figure 10B:
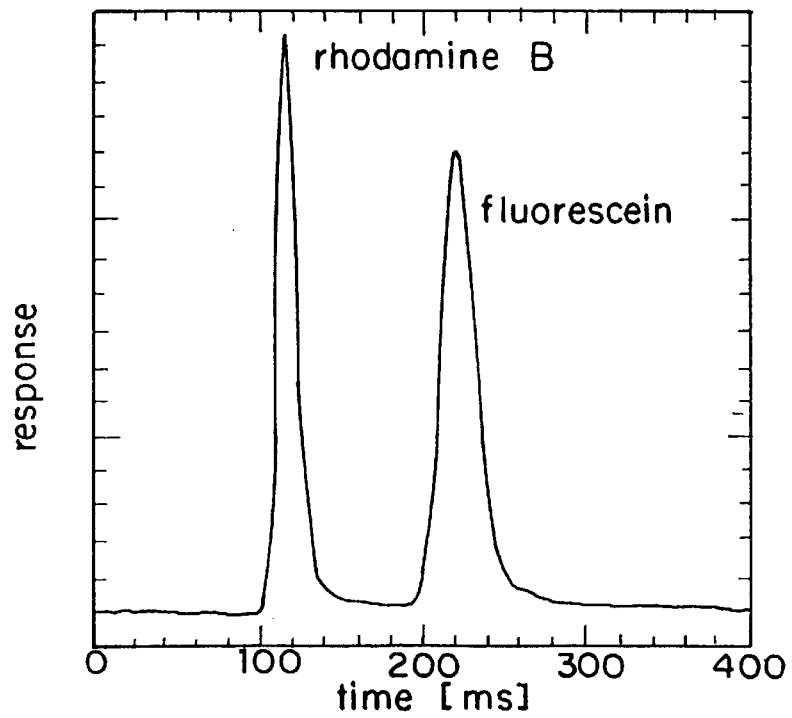
FIG. 10(b) is an electropherogram of rhodamine B and fluorescein with a separation field strength of 1.5 kV/cm and a separation length of 1.6 mm.
Figure 10C:
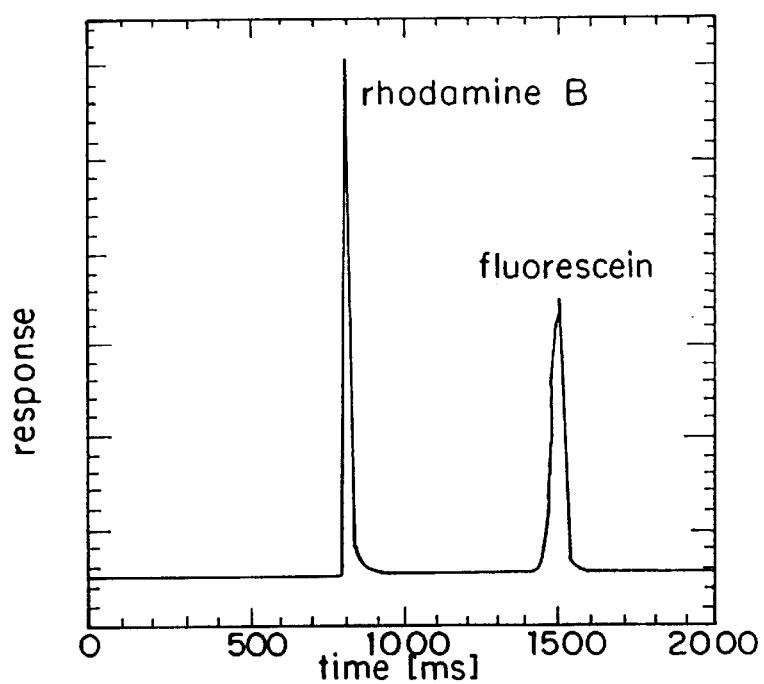
FIG. 10(c) is an electropherogram of rhodamine B and fluorescein with a separation field strength of 1.5 kV/cm and a separation length of 11.1 mm.

One particular advantage to the planar microchip 20 of the present invention is that with laser induced fluorescence the point of detection can be placed anywhere along the separation column. The electropherograms are detected at separation lengths of 0.9 mm, 1.6 mm and 11.1 mm from the injection intersection 46. The 1.6 mm and 11.1 mm separation lengths were used over a range of electric field strengths from 0.06 to 1.5 kV/cm, and the separations had baseline resolution over this range. At an electric field strength of 1.5 kV/cm, the analytes, rhodamine B and fluorescein, are resolved in less than 150 ms for the 0.9 mm separation length, as shown in FIG. 10(a), in less than 260 ms for the 1.6 mm separation length, as shown in FIG. 10(b), and in less than 1.6 seconds for the 11.1 mm separation length, as shown in FIG. 10(c).

Due to the trapezoidal geometry of the channels, the upper corners make it difficult to cut the sample plug away exactly when the potentials are switched from the sample loading mode to the separation mode. Thus, the injection plug has a slight tail associated with it, and this effect probably accounts for the tailing observed in the separated peaks.

An important measure of the utility of a separation system is the number of plates generated per unit time, as given by the formula $$N/t=L/(Ht)$$

where N is the number of theoretical plates, t is the separation time, L is the length of the separation column, and H is the height equivalent to a theoretical plate. The plate height, H, can be written as $$H=A+B/u$$

where A is the sum of the contributions from the injection plug length and the detector path length, B is equal to $2_{Dm}$, where $D_m$ is the diffusion coefficient for the analyte in the buffer, and u is the linear velocity of the analyte.

Combining the two equations above and substituting u=μE where μ is the effective electrophoretic mobility of the analyte and E is the electric field strength, the plates per unit time can be expressed as a function of the electric field strength:

$$N/t=(\mu E)^2/(A\mu E+B)$$

At low electric field strengths when axial diffusion is the dominant form of band dispersion, the term $A\mu E$ is small relative to B and consequently, the number of plates per second increases with the square of the electric field strength.

As the electric field strength increases, the plate height approaches a constant value, and the plates per unit time increases linearly with the electric field strength because B is small relative to $A\mu E$. It is thus advantageous to have A as small as possible, a benefit of the pinched injection scheme.

Figure 11:
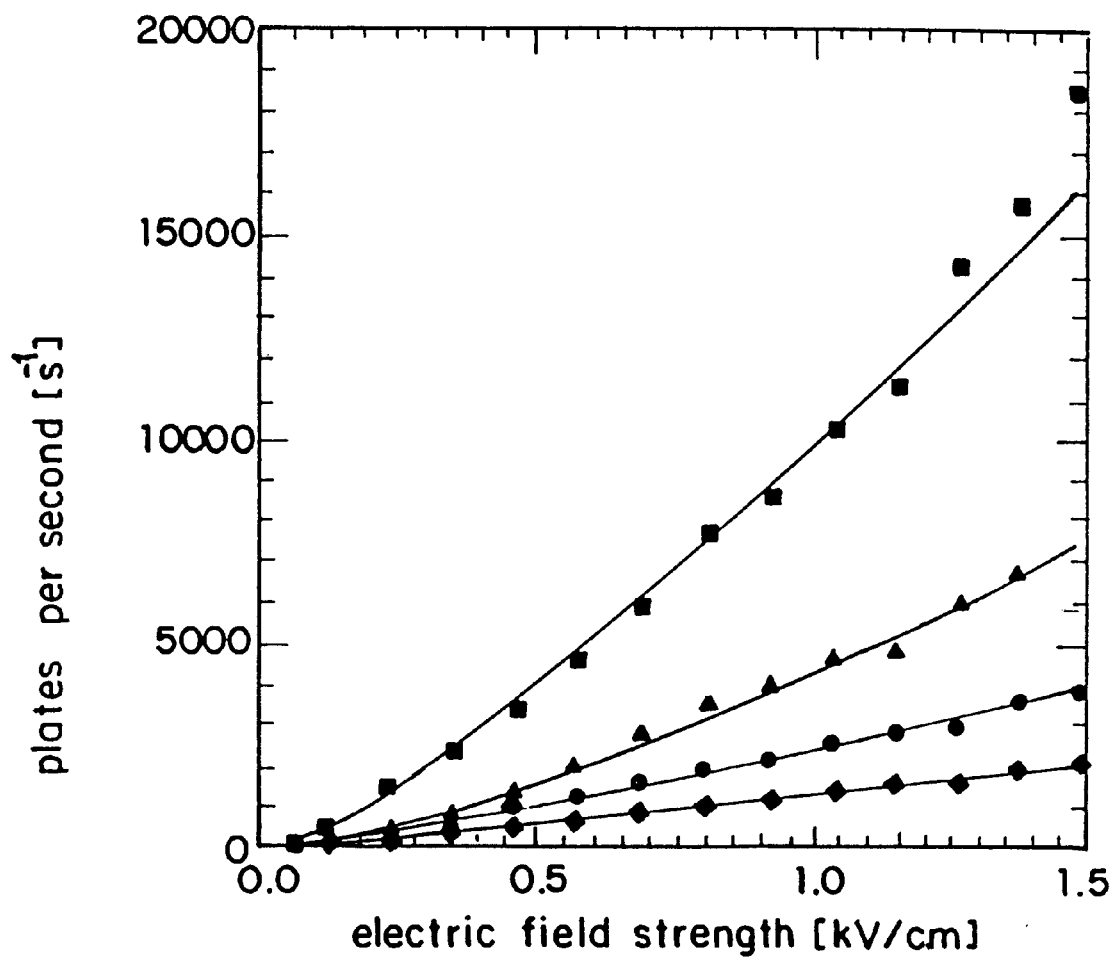
FIG. 11 is a graph showing variation of the number of plates per unit time as a function of the electric field strength for rhodamine B at separations lengths of 1.6 mm (circle) and 11.1 mm (square) and for fluorescein at separation lengths of 1.6 mm (diamond) and 11.1 mm (triangle)

In FIG. 11, the number of plates per second for the 1.6 mm and 11.1 mm separation lengths are plotted versus the electric field strength. The number of plates per second quickly becomes a linear function of the electric field strength, because the plate height approaches a constant value. The symbols in FIG. 11 represent the experimental data collected for the two analytes at the 1.6 mm and 11.1 mm separation lengths. The lines are calculated using the previously-stated equation and the coefficients are experimentally determined. A slight deviation is seen between the experimental data and the calculated numbers for rhodamine B at the 11.1 mm separation length. This is primarily due to experimental error.

There are situations where it may not be desirable to reverse the flow in the separation channel as described above for the "pinched" and "floating" injection schemes. Examples of such cases might be the injection of a new sample plug before the preceding plug has been completely eluted or the use of a post-column reactor where reagent is continuously being injected into the end of the separation column. In the latter case, it would in general not be desirable to have the reagent flowing back up into the separation channel.

Figure 12:
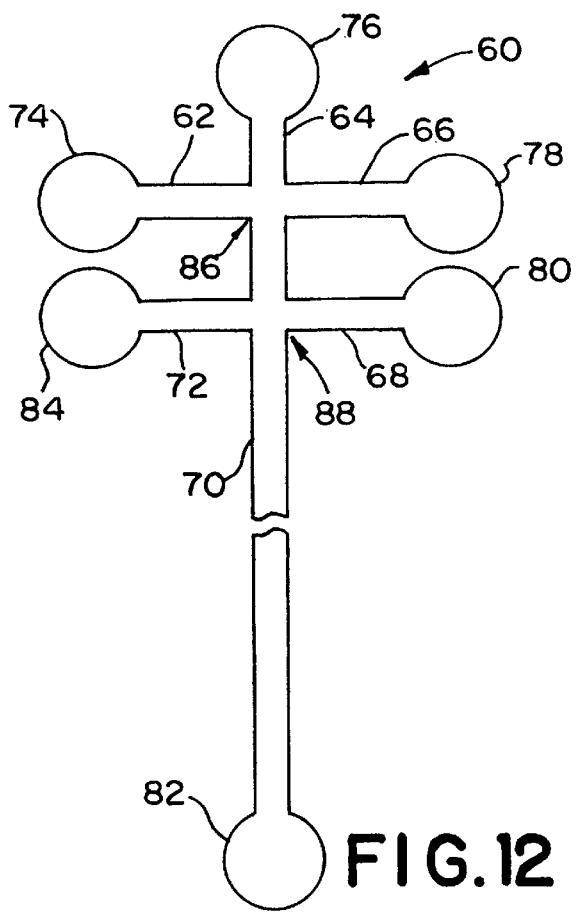
FIG. 12 is a schematic, top view of a microchip according to another embodiment of the present invention.

FIG. 12 illustrates a microchip 60 having six different ports or channels 62, 64, 66, 68, 70, and 72 respectively connected to six different reservoirs 74, 76, 78, 80, 82, and 84. The microchip 60 is similar to microchips 20 and 20' described previously, in that an injection cross or intersection 86 is provided. In the FIG. 12 embodiment, a second intersection 88 and two additional buffer reservoirs 80 and 84 are also provided.

As in the previous embodiments, reservoir 76 contains separating buffer, reservoir 74 contains the sample to be analyzed (the "analyte"), and reservoirs 78 and 82 are waste reservoirs. Intersection 86 is operated in the pinched mode as in the previous embodiments. The lower intersection 88, in fluid communication with reservoirs 80 and 84, are used to make up additional flow so that a continuous buffer stream can be directed down towards the waste reservoir 82 and, when needed, upwards toward the injection intersection 86. Reservoir 84 and attached channel 72 are not necessary, although they improve performance by reducing band broadening as a plug passes the lower intersection 88. In all cases, the flow from reservoir 84 will be symmetric with that from reservoir 80.

Figure 13:
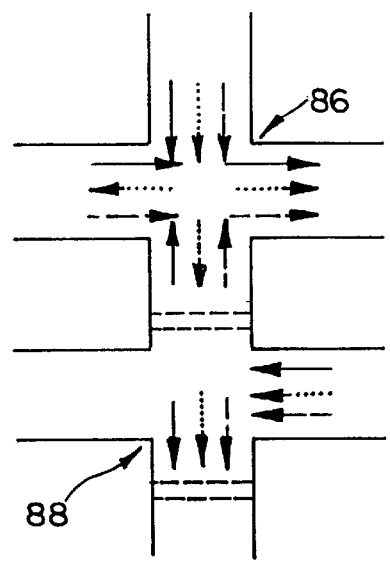
FIG. 13 is an enlarged view of the intersection region of FIG. 12.

FIG. 13 is an enlarged view of the two intersections 86 and 88. The different types of arrows show the flow directions at given instances in time for injection of a plug of sample into the separation channel. The solid arrows show the initial flow pattern where sample is electroosmotically pumped into the upper intersection 86 and "pinched" by flow from reservoirs 76 and 80 toward this same intersection. Flow away from this intersection is carried to the sample waste reservoir 78. The sample is also flowing from the reservoir 74 to the waste reservoir 78. Under these conditions, flow from reservoir 80 (and reservoir 84) is also going down the separation channel 70 to the waste reservoir 82.

A plug of sample is injected by switching to the flow profile shown by the short dashed arrows. Buffer flows down from reservoir 76 to the upper intersection 86 and towards reservoirs 74, 78 and 82. This flow profile also pushes a plug of sample toward waste reservoir 82 into the separation channel 70 as described before.

This flow profile is held for a sufficient length of time so as to move the sample plug past the lower intersection. The flow of buffer from reservoirs 80 and 84 should be low as indicated by the short arrow and into the separation channel 70 to minimize distortion.

The distance between the upper and lower intersections 86 and 88, respectively, should be as small as possible to minimize plug distortion and criticality of timing in the switching between the two flow conditions. Electrodes for sensing the electric potential might also be placed at the lower intersection and in the channel 68 to assist in adjusting the electric potentials for proper flow control. Accurate flow control at the lower intersection 88 may be necessary to prevent unacceptable band broadening.

After the sample plug passes the lower intersection, the potentials are switched back to the initial conditions to give the original flow profile as shown with the long dashed arrows. This flow pattern will allow buffer flow into the separation channel 70 while sample is again being transported to the plug forming region in the upper intersection 86. This injection scheme will allow more rapid injections to be made and may be very important for samples that are slow to migrate or if it takes a long time to achieve a homogeneous sample at the upper intersection 86 such as with entangled polymer solutions.

Figure 14:
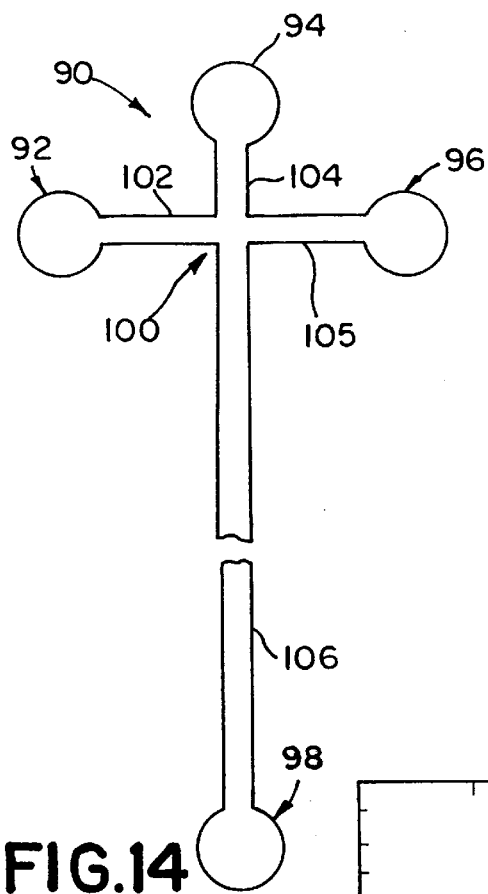
FIG. 14 is a schematic, top view of a microchip according to another embodiment of the present invention.

A different approach to injection can be taken with a four leg or cross-type injector. It also provides a continuous unidirectional flow of fluid through the separation channel. This injection scheme only requires that the voltage be changed or removed from one (or two) reservoirs and allows the separation channel waste reservoir to remain at ground potential. This will allow injection and separation to be performed with a single polarity power supply. Referring to FIG. 14, a microchip 90 includes a buffer reservoir 92, a sample reservoir 94, a sample waste reservoir 96, and a separation channel waste reservoir 98. An intersection 100 is formed at the confluence of buffer channel 102, sample channel 104, sample waste channel 105, and the separation channel 106.

Figure 15:
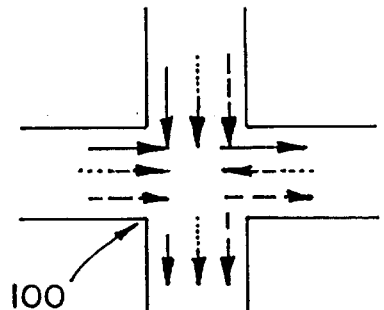
FIG. 15 is an enlarged view of the intersection region of FIG. 14.

An enlarged view of the intersection 100 is shown in FIG. 15. The directional arrows indicate the time sequence of the flow profiles at the intersection 100. The solid arrows show the initial flow pattern. Voltages at the various reservoirs are adjusted to obtain the described flow patterns. The initial flow pattern brings buffer from reservoir 92 at a sufficient rate such that all sample is pushed toward the sample waste reservoir 96. Under these conditions, the flow towards reservoir 98 is pure buffer.

In general, the potential distribution will be such that the highest potential is at reservoir 92, a slightly lower potential at reservoir 94 and yet a lower potential at reservoir 96, with reservoir 98 being grounded. To make an injection of sample, the potential at reservoir 96 can be switched to a higher value or the potentials at reservoirs 92 and 96, or 96 only, can be floated momentarily to provide the flow shown by the short dashed arrows in FIG. 15.

Under these conditions, the primary flow will be from the sample reservoir 92 down towards the separation channel waste reservoir 98. The flow from reservoirs 92 and 96 will be small and in practice in either direction. This condition is held only long enough to pump a sample plug into the separation channel. After sufficient time for sample injection, the voltage distribution is switched back to the original values eliminating sample from flowing toward the separation channel 106. After sufficient time for sample injection, the voltage distribution is switched back to the original values, thus eliminating sample from flowing toward the separation channel 106.

The type of sample injector described with respect to FIGS. 14 and 15 show electrophoretic mobility based bias as do conventional electroosmotic injections. In addition, this injection approach is time dependent unlike the pinched injection approach described above. Nonetheless, this approach has simplicity in voltage switching requirements and fabrication.

The "four port" configuration of FIG. 14 provides continuous unidirectional flow through the separation channel 106. A schematic view of the microchip 90 is shown in FIG. 16. The four-port pattern of channels is disposed on a glass substrate 108 and glass cover slip 110, as in the previously-described embodiments.

Sample channel 104 is in one embodiment 2.7 mm in length from the sample reservoir 94 to the intersection 100, while sample waste channel 105 is 6.5 mm, and buffer channel 102 is 7.0 mm. The separation channel 106 is modified to be only 7.0 mm in length, due to the addition of a reagent reservoir 112 which has a reagent channel 114 that connects to the separation channel 106 at a mixing tee 116. Thus, the length of the separation channel 106 is measured from the intersection 100 to the mixing tee 116.

The channel 118 extending from the mixing tee 116 to the waste reservoir 98 is the reaction column or channel, and in the illustrated embodiment this channel is 10.8 mm in length. The length of channel 114 is 11.6 mm.

Because the substrate 108 is glass and the channels are chemically wet etched, an isotropic etch occurs, i.e., the glass etches uniformly in all directions, and the resulting channel geometry is trapezoidal. The channel cross section of the illustrated embodiment has dimensions of 5.2 $\mu$m in depth, 57 $\mu$m in width at the top and 45 $\mu$m in width at the bottom.

While glass is a preferred material, other similar materials may be used, such as fused silica, crystalline quartz, and silicon (if surface treated to alter its resistivity).

Column performance and separations using the FIG. 16 embodiment were monitored on-microchip via fluorescence using an argon ion laser (351.1 nm, 50 mW, Coherent Innova 90) for excitation. The fluorescence signal was collected with a photomultiplier tube (PMT, Oriel 77340) for point detection and a charge coupled device (CCD, Princeton Instruments, Inc. TE/CCD-512 TKM) for imaging a region of the microchip 90. The compounds used for testing the apparatus were rhodamine B (Exciton Chemical Co., Inc.) arginine, glycine, threonine and o-phthaldialdehyde (Sigma Chemical Co.). A sodium tetraborate buffer (20 mM, pH 9.2) with 2% (v/v) methanol and 0.5% (v/v) β-mercaptoethanol was the buffer in all tests. The concentrations of the amino acid, OPA and rhodamine B solutions were 2 mN, 3.7 mN, and 50 $\mu$M, respectively. Several run conditions were utilized.

To inject a small aliquot of sample, the potentials at the buffer and analyte waste reservoir are simply floated for a short period of time ($\approx$100 ms) allowing sample to migrate down the separation column 106 as in an WP injection. To break off the injection plug, the potentials at the buffer reservoir 92 and the sample (or analyze) waste reservoir 96 are re-applied. A shortfall of this method is that the composition of the injected plug has an D bias whereby the faster migrating compounds are introduced preferentially into the separation column 106 over slower migrating compounds.

Figure 17:
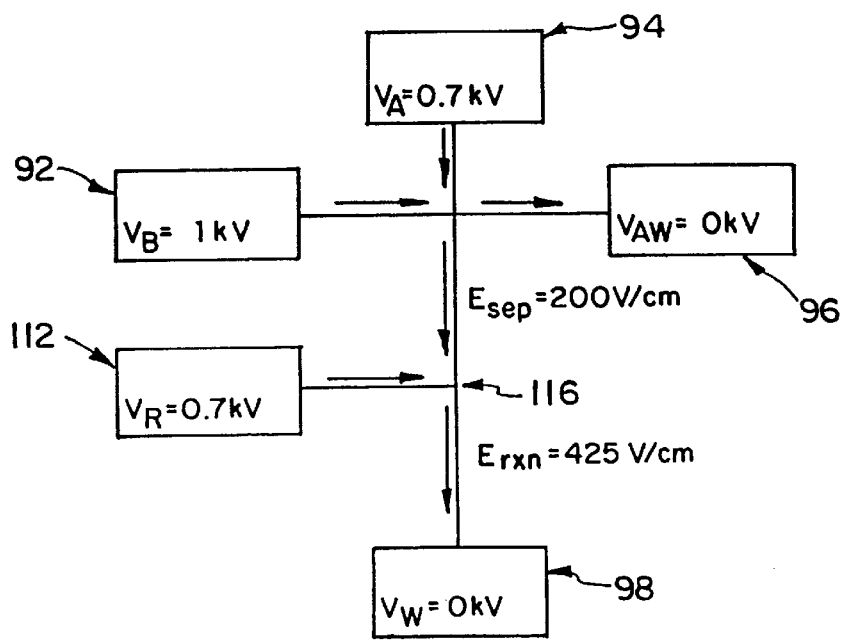
FIG. 17 is a schematic view of the embodiment of FIG. 16, showing applied voltages.

The schematic view in FIG. 17 demonstrates one example when 1 kV is applied to the entire system. With this voltage configuration, the electric field strengths in the separation column ($E_{sep}$) and the reaction column ($E_{rxn}$) are 200 and 425 V/cm, respectively. This allows the combining of 1 part separation effluent with 1.125 parts reagent at the mixing tee 116. A sample introduction system such as this, with or without post-column reaction, allows a very rapid cycle time for multiple analyses.

Figures 18A, 18B, 18C:
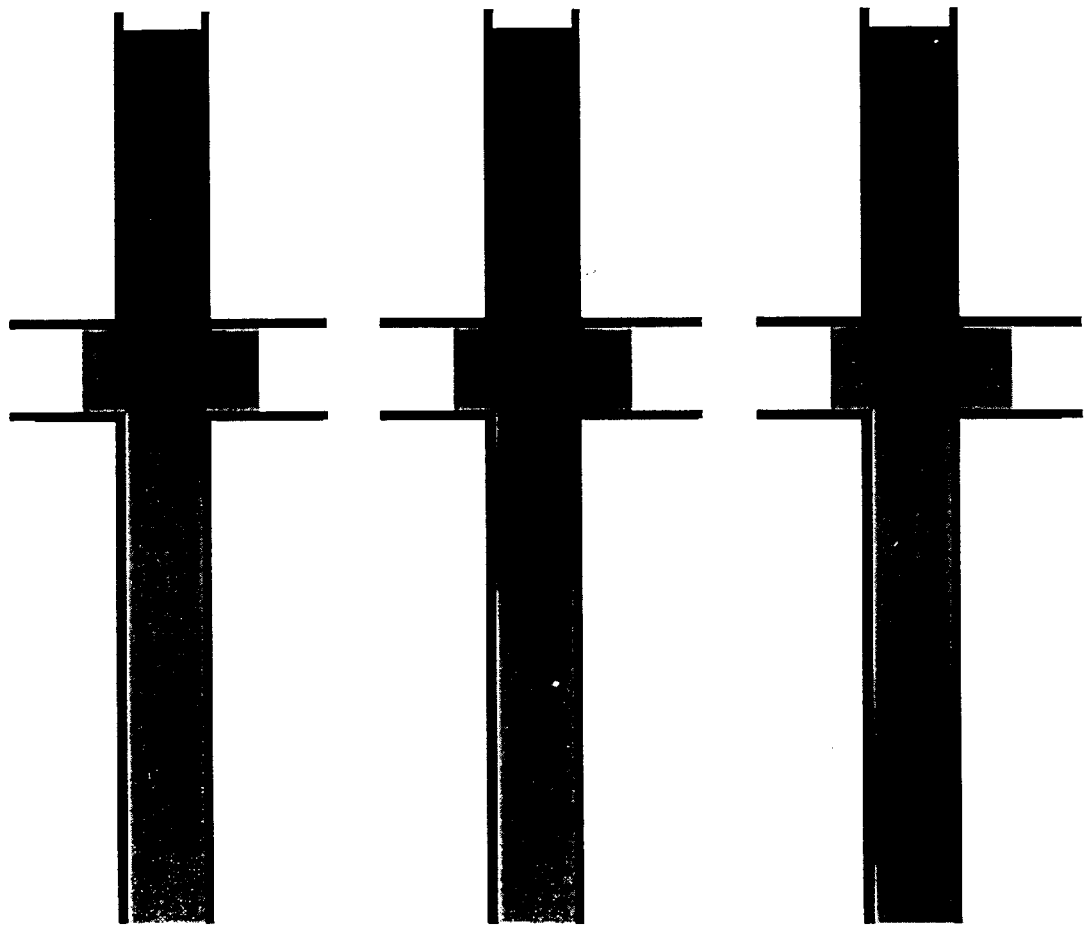
FIG. 18 are CCD images of a plug of analyte moving through the intersection of the FIG. 16 embodiment.

In FIG. 18, a sequential view of a plug of analyze moving through the intersection of the FIG. 16 embodiment can be seen by CCD, using the potentials illustrated in FIG. 17. The analyze being pumped through the microchip 90 was rhodamine B (shaded area), and the orientation of the CCD images of the injection cross is the same as in FIGS. 12 and 17. The first image, (A), shows the analyze being pumped through the injection cross or intersection toward the sample waste reservoir 96 prior to the injection. The second image, (B), catches the analyze plug being broken away from the analyze stream and being injected into the separation column. The third image, (C), depicts the analyze plug moving away from the injection cross after an injection plug has been completely introduced into the separation column. The potentials at the buffer and analyze waste reservoirs were floated for 100 ms while the sample moved into the separation column. By the time of the (C) sequence, the loading/separation mode has resumed, and a clean injection plug with a length of 142 $\mu$m has been introduced into the separation column. As seen below, the gated injector contributes to only a minor fraction of the total plate height. The injection plug length is a function of the time of the injection and the electric field strength in the column. The shape of the injected plug is skewed slightly because of the directionality of the cleaving buffer flow. However, for a given injection period, the reproducibility of the amount injected, determined by integrating the peak area, is 1% RSD for a series of 10 replicate injections.

Figure 19A:
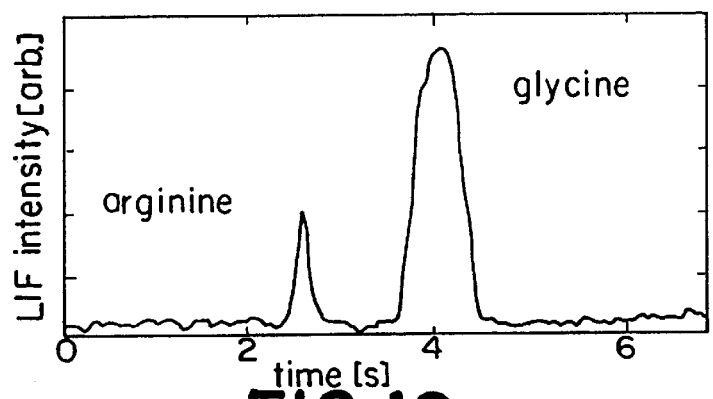
FIG. 19 show two electropherograms producing using the FIG. 16 embodiment.
Figure 19B:
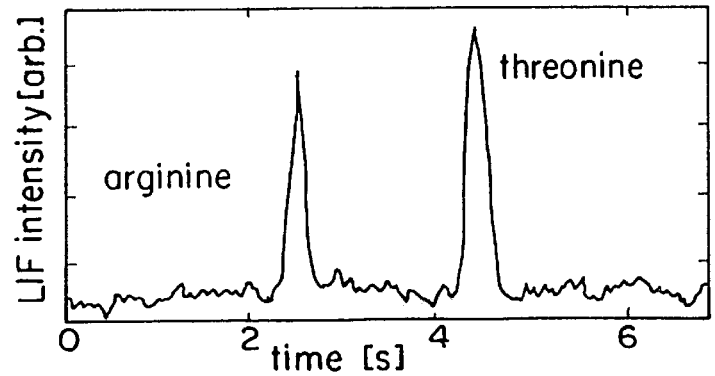

The electropherograms (A) and (B) in FIG. 19 demonstrate the separation of two pairs of amino acids. The voltage configuration is the same as in FIG. 17, except the total applied voltage is 4 kV which corresponds to an electric field strength of 800 V/cm in the separation column ($E_{sep}$) and 1,700 V/cm in the reaction column ($E_{rxn}$). The injection times were 100 ms for the tests which correspond to estimated injection plug lengths of 384, 245, and 225 $\mu$m for arginine, glycine and threonine, respectively. The injection volumes of 102, 65, and 60 pL correspond to 200, 130, and 120 fmol injected for arginine, glycine and threonine, respectively. The point of detection is 6.5 mm downstream from the mixing tee which gives a total column length of 13.5 mm for the separation and reaction.

The reaction rates of the amino acids with the OPA are moderately fast, but not fast enough on the time scale of these experiments. An increase in the band distortion is observed because the mobilities of the derivatized compounds are different from the pure amino acids. Until the reaction is complete, the zones of unreacted and reacted amino acid will move at different velocities causing a broadening of the analyze zone. As evidenced in FIG. 19, glycine has the greatest discrepancy in electrophoretic mobilities between the derivatized and un-derivatized amino acid. To ensure that the excessive band broadening was not a function of the retention time, threonine was also tested. Threonine has a slightly longer retention time than the glycine; however, the broadening is not as extensive as for glycine.

The present invention can be used to mix different fluids contained in different ports or reservoirs. This could be used for a liquid chromatography separation experiment followed by post-column labeling reactions in which different chemical solutions of a given volume are pumped into the primary separation channel and other reagents or solutions can be injected or pumped into the stream at different times to be mixed in precise and known concentrations. To execute this process, it is necessary to accurately control and manipulate solutions in the various channels.

The use of electroosmotic flow on microminiaturized planar liquid phase separation devices, described above, is a viable approach for sample manipulation and as a pumping mechanism for liquid chromatography. The present invention also entails the use of electroosmotic flow can also be used to mix various fluids in a controlled and reproducible fashion. When an appropriate fluid is placed in a tube made of a correspondingly appropriate material, functional groups at the surface of the tube can ionize. In the case of tubing materials that are terminated in hydroxyl groups, protons will leave the surface and enter an aqueous solvent. Under such conditions the surface will have a net negative charge and the solvent will have an excess of positive charges. With the application of an electric field across the tube, the excess cations in solution will be attracted to the cathode, or negative electrode. The movement of these positive charges through the tube will drag the solvent with them. The steady state velocity is given by equation 1, $$v = \frac{\epsilon \times \xi \times E}{\pi}$$

where v is the solvent velocity, $\epsilon$ is the dielectric constant of the fluid, $\xi$ is the zeta potential of the surface, E is the electric field strength, and, is the solvent viscosity. From equation 1 it is obvious that the fluid flow velocity or flow rate can be controlled through the electric field strength. Thus, electroosmosis can be used as a programmable pumping mechanism.

Figure 20:
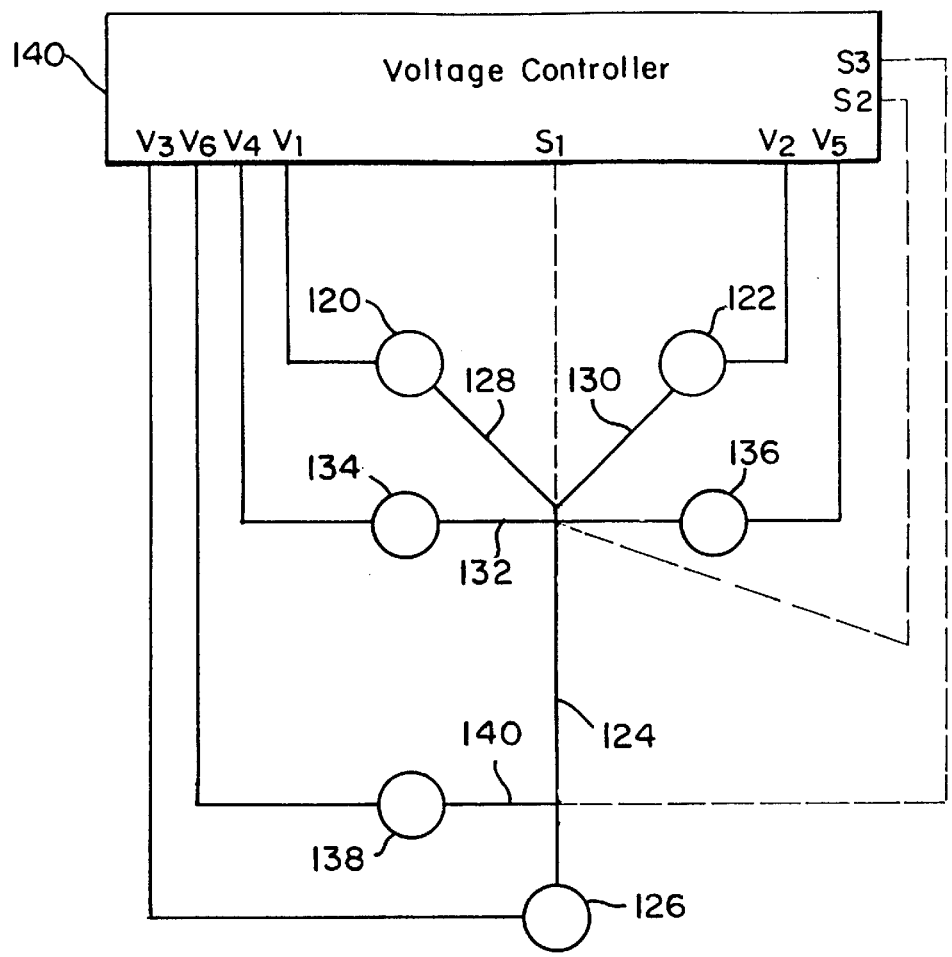
FIG. 20 is a schematic view of another preferred embodiment of the present invention.

FIG. 20 shows a six port device that could take advantage of this novel mixing scheme. Particular features attached to the different ports represent solvent reservoirs. This device could potentially be used for a liquid chromatography separation experiment followed by post-column labeling reactions. On such a device, reservoirs 120 and 122 would contain solvents to be used in a liquid chromatography solvent programming type of separation.

The channel 124 connected to waste reservoir 126, and to the two arms 128 and 130 of reservoirs 120 and 122 is the primary separation channel, i.e., where the liquid chromatography experiment would take place. The intersecting channel 132 connecting reservoirs 134 and 136 is used to make an injection into the liquid chromatography or separation channel 124. Finally, reservoir 138 and its channel 140 attaching to the separation channel 124 is adding a reagent, which is added in proportions to render the species separated in the separation channel detectable.

To execute this process, it is necessary to accurately control and manipulate solutions in the various channels. The embodiments described above took very small volumes of solution ($\approx$100 pl) from reservoir 134 and accurately injected them into the separation channel structure.

For these various scenarios, a given volume of solution needs to be transferred from one channel to another. For example, solvent programming for liquid chromatography or reagent addition for post-column labeling reactions requires that streams of solutions be mixed in precise and known concentrations.

The mixing of various solvents in known proportions can be done according to the present invention by controlling potentials which ultimately control electroosmotic flows as indicated in equation 1. According to equation 1 the electric field strength needs to be known to determine the linear velocity of the solvent. In general, in these types of fluidic manipulations a known potential or voltage is applied to a given reservoir. The field strength can be calculated from the applied voltage and the characteristics of the channel. In addition, the resistance or conductance of the fluid in the channels must also be known. The resistance of a channel is given by equation 2 where R is the resistance, p is the resistivity, L is the length of the channel, and A is the cross-sectional area.

$$R_i = \frac{\rho_i L_i}{A_i}$$

Fluids are usually characterized by conductance which is just the reciprocal of the resistance as shown in equation 3. In equation 3, K is the electrical conductance, $\rho$ is the conductivity, A is the cross-sectional area, and L is the length as above.

$$K_i = \frac{\kappa_i A_i}{L_i}$$

Using ohms law and equations 2 and 3 we can write the field strength in a given channel, i, in terms of the voltage drop across that channel divided by its length which is equal to the current, $I_i$ through channel i times the resistivity of that channel divided by the cross-sectional area as shown in equation 4.

$$E_i = \frac{V_i}{L_i} = \frac{I_i \rho_i}{A_i} = \frac{I_i}{\kappa_i A_i}$$

Thus, if the channel is both dimensionally and electrically characterized, the voltage drop across the channel or the current through the channel can be used to determine the solvent velocity or flow rate through that channel as expressed in equation 5.

$$V_i I_i \text{ Flow}$$

Obviously the conductivity, $\kappa$ or the resistivity, p, will depend upon the characteristics of the solution which could vary from channel to channel. In many CE applications the characteristics of the buffer will dominate the electrical characteristics of the fluid, and thus the conductance will be constant. In the case of liquid chromatography where solvent programming is performed, the electrical characteristics of the two mobile phases could differ considerably if a buffer is not used. During a solvent programming run where the mole fraction of the mixture is changing, the conductivity of the mixture may change in a nonlinear fashion but it will change monotonically from the conductivity of the one neat solvent to the other. The actual variation of the conductance with mole fraction depends on the dissociation constant of the solvent in addition to the conductivity of the individual ions.

As described above, the device shown schematically in FIG. 20 could be used for performing gradient elution liquid chromatography with post-column labeling for detection purposes, for example. In order to carry out such a task using electroosmotic manipulation of fluids, a voltage control 140 must be used to control the electric potentials applied to each of the solvent reservoirs. It may also be desirable to monitor potentials at given positions, for example at channel cross sections, so that there is additional information for intelligent control of the various reservoir potentials and thus fluid flow. These control signals and electrical connections are denoted by the symbols S1, S2 and S3 and the corresponding broken lines. The voltage controller box shown in FIG. 20 is programmed to change the voltages as a function of time to carry out various tasks.

FIG. 21 shows the fluid flow requirements for carrying out the tasks involved in a liquid chromatography experiment as mentioned above. The arrows in the figures show the direction and relative magnitude of the flow in the channels. The first task, inject "a", is an injection of a volume of sample from reservoir 4 into the separation channel. To execute a pinched injection it is necessary to transport the sample from reservoir 4 across the intersection to reservoir 5. In addition, to confine the sample volume, fluid flow from the separation channel and the solvent reservoirs must flow towards the intersection as shown. The flow from reservoir 1 is much larger than that from reservoir 2 because these are the initial conditions for a gradient elution experiment.

It is also desirable to prevent the reagent in reservoir 6 from entering the separation channel, thus, a small flow of buffer directed toward the reagent channel is desirable and this flow should be as near to zero as possible. After a representative sample is presented at the injection intersection, the separation can proceed. In "b" the start of a run (separation), solvent from reservoirs 1 and 2 flows down the separation channel and also towards reservoirs 4 and 5 to make a clean injection of sample into the separation column.

Appropriate flow of reagent from reservoir 6 is also directed towards the separation channel. The initial condition as shown in "b" is with a large mole fraction of solvent 1 and a applied to reservoirs 1 and 2 are changed as a function of time so that the proportions of solvents 1 and 2 are changed from a dominance of solvent 1 to mostly solvent 2. This is seen in "c". The latter monotonic change in applied voltage effects the gradient elution liquid chromatography experiment. As the isolated components pass the reagent addition channel, appropriate reaction can take place between this reagent and the isolated material to form a detectable species.

Figure 22:
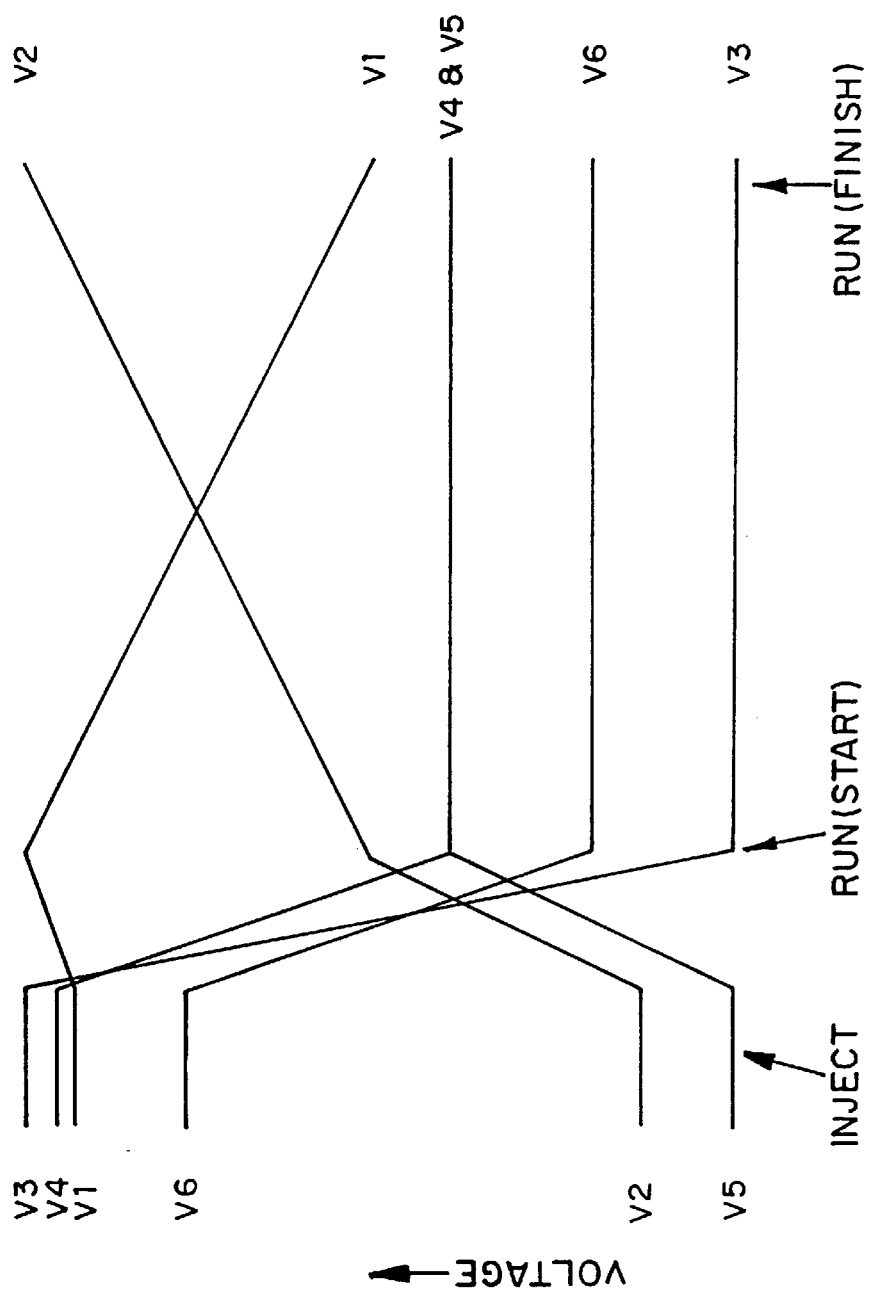
FIG. 22 is a graph showing the different voltages applied to effect the fluidic manipulations of FIG. 21.

FIG. 22 shows how the voltages to the various reservoirs are changed for a hypothetical experiment. The voltages shown in this diagram are only to indicate relative magnitudes and not absolute voltages. In the injection mode of operation static voltages are applied to the various reservoirs. Solvent flow from all reservoirs except reservoir 6 is towards the sample waste reservoir 5. Thus, reservoir 5 is at the lowest potential and all the other reservoirs are at higher potential. The potential at reservoir 6 should be sufficiently below that of reservoir 3 to provide only a slight flow towards reservoir 6. The voltage at reservoir 2 should be sufficiently great in magnitude to provide a net flow towards the injection intersection, but the flow should be a low magnitude.

In moving to the run (start) mode, the potentials are readjusted as indicated in FIG. 22. The flow now is such that the solvent from reservoirs 1 and 2 is moving down the separation channel towards reservoir 3. There is also a slight flow of solvent away from the injection cross towards reservoirs 4 and 5 and an appropriate flow of reagent from reservoir 6 into the separation channel. Reservoir 3 now needs to be at the minimum potential and reservoir 1 at the maximum potential. All other potentials are adjusted to provide the fluid flow directions and magnitudes as indicated in FIG. 21 at "b". Also as shown in FIG. 22 the voltages applied to the solvent reservoirs 1 and 2 are monotonically changed to move from the conditions of a large mole fraction of solvent 1 to a large mole fraction of solvent 2.

At the end of the solvent programming run, the device is now ready to switch back to the inject condition to load another sample. The voltage variations shown in FIG. 22 are only to be illustrative of what might be done to provide the various fluid flows in FIG. 21. In an actual experiment some to the various voltages may well differ in relative magnitude.

For capillary separation systems, the small detection volumes can limit the number of detection schemes which can be used to extract information. Fluorescence detection remains one of the most sensitive detection techniques for capillary electrophoresis. When incorporating fluorescence detection into a system that does not have naturally fluorescing analytes, derivatization of the analyze must occur either pre-or post-separation. When the fluorescent "tag" is short lived or the separation is hindered by pre-separation derivatization, post-column addition of derivatizing reagent becomes the method of choice. A variety of post-column reactors have been demonstrated for capillary electrophoresis. However, the ability to construct a post-column reactor with extremely low volume connections to minimize band distortion has been difficult. The present invention takes the approach of fabricating a microchip device for electrophoretic separations with post-column and reaction column can be coupled in a single monolithic device enabling extremely low volume exchanges between individual column functions. This microfabrication approach is a part of the continuing effort toward micromachining of miniaturized instrumentation of chemical separations which includes devices for gas chromatography, liquid chromatography, and capillary electrophoresis.

The microchip for the FIG. 20 embodiment was fabricated using standard photolithographic, wet chemical etching, and bonding techniques. A photomask was fabricated by sputtering chrome (50 nm) onto a glass slide and ablating the column design into the chrome film via a CAD/CAM laser ablation system (Resonetics, Inc.). The column design was then transferred onto the substrates using a positive photoresist. The channels were etched into the substrate in a dilute $Hf/Nh_4F$ bath. To form the separation capillary, a coverplate was bonded to the substrate over the etched channels using a direct bonding technique. The surfaces were hydrolyzed in dilute $NH_4OH/H_2O_2$ solution, rinsed in deionized, filtered $H_2$, joined and then annealed at 500° C. Cylindrical glass reservoirs were affixed on the substrate using RTV silicone (made by General Electric). Platinum electrodes provided electrical contact from the power supply (Spellman CZE1000R) to the solutions in the reservoirs.

Column performance and separations were monitored on-microchip via fluorescence using an argon ion laser (35.1 nm, 50 mW, Coherent Innova 90) for excitation. The fluorescence signal was collected with a photomultiplier tube (PMT; Oriel 77340) for point detection and a charge coupled device (CCD; Princeton Instruments, Inc. TE/CCD-512 TKM) for imaging a region of the microchip. The compounds used for the experiments were rhodamine B (Exciton Chemical Co., Inc.), arginine, glycine, threonine and o-phthaldialdehyde (Sigma Chemical Co.). A sodium tetraborate buffer (20 mM, pH 9.2) with 2% (v/v) methanol and 0.5% (v/v) β-mercaptoethanol was the buffer in all experiments. the concentrations of the amino acid, OPA and rhodamine B solutions were 2 mN, 3.7 mN, and 50 μM, respectively. Several run conditions were utilized for microchip diagnostics and will be described as needed.

Because several separation lengths were used to study different aspects of the microchip performance, the efficiencies will be reported primarily using the plate height (H). The contributions to the plate height are:

$$H = H_{diff} + H_{inj} + H_{det} = 2D_m/u + 1_{inj}^2/(12 L_{sep}) + 1_{det}^2/(12 L_{sep})$$

where $H_{diff}$, $H_{inj}$ and $H_{det}$ are the contributions of axial diffusion, injection plug length, and detector observation length to the plate height, respectively. $D_m$ is the diffusion coefficient of th analyze in the buffer, u is the linear velocity of the analyze, $1_{inj}$ is the injection plug length, $1_{det}$ is the detector observation length, and $L_{sep}$ is the separation length. The effect of Joule heating were not considered because the power dissipation was below 1 W/m for all experiments. The contribution from the axial diffusion is time dependent, and the contributions from the injection plug length and detector observation length are time independent. In electrophoretic separations, the linear velocity of the analyze, u, is equal to the product of the effective electrophoretic mobility, $\mu_{ep}$, and the electric field strength, E.

To test the efficiency of the microchip in both the separation column and the reaction column, a fluorescent laser dye, rhodamine B, was used as a probe. Efficiency measurements calculated from peak widths at half height were made using the point detection scheme at distances of 6 mm and 8 mm from the injection cross, or 1 mm upstream and 1 mm downstream from the mixing tee. This provided information on the effects of the mixing of the two streams.

The electric field strengths in the reagent column and the separation column were approximately equal, and the field strength in the reaction column was twice that of the separation column. This configuration of the applied voltages allowed an approximately 1:1 volume ratio of derivatizing reagent and effluent from the separation column. As the field strengths increased, the degree of turbulence at the mixing tee increased. At the separation distance of 6 mm (1 mm upstream from the mixing tee), the plate height data decreased as expected as the inverse of the linear velocity of the analyze (Equation 6). At the separation distance of 8 mm (1 mm upstream from the mixing tee), the plate height data decreased as expected as the inverse of the linear velocity of the analyze (Equation 6). At the separation distance of 8 mm (1 mm downstream from the mixing tee), the plate height data decreases from 140 V/cm to 280 V/cm to 1400 V/cm. This behavior is abnormal (Equation 6) and demonstrates a band broadening phenomena when two streams of equal volumes converge. The geometry of the mixing tee was not optimized to minimize this band distortion. Above separation field strength of 840 V/cm, the system stabilizes and again the plate height decreases with increasing linear velocity. For $E_{sep}$=1400 V/cm, the ratio of the plate heights at the 8 mm and 6 mm separation lengths is 1.22 which is not an unacceptable loss in efficiency for the separation.

Following the combining of the two streams at the mixing tee, the intensity of the fluorescence signal generated from the reaction of the OPA with an amino acid was tested by pumping glycine down the column as a frontal electropherogram to mix with the OPA at the mixing tee. The fluorescence signal from the OPA/amino acid reaction was collected using a CCD as the product moved downstream from the mixing tee. Again, the relative volume ratio of the OPA and glycine streams was 1.125. OPA has a typical half-time of reaction with amino acids of 4 s. The average residence times of an analyze molecule in the window of observation are 4.68, 2.34, 1.17, and 0.58 s for the electric field strengths in the reaction column ($E_{rxn}$) of 240, 480, 960, and 1920 V/cm, respectively. The relative intensities of the fluorescence correspond qualitatively to this 4 s half-time of reaction. As the field strength increases in the reaction column, the slope and maximum of the intensity of the fluorescence shifts further downstream because the glycine and OPA are swept away from the mixing tee faster with higher field strengths. Ideally, the observed fluorescence from the product would have a step function of ra response following the mixing of the separation effluent and derivatizing reagent. However, the kinetics of the reaction and a finite rate of mixing dominated by diffusion prevent this from occurring.

The use of the post-column reactor required a different injection scheme than the pinched injection in order to keep the analyze, buffer and reagent streams isolated. For the post-column reaction separations, the microchip was operated in a continuous sample loading/separation mode whereby the sample was continuously pumped from the analyze reservoir through the injection cross toward the analyze waste reservoir. Buffer was simultaneously pumped from the buffer reservoir toward the analyze waste and waste reservoirs to deflect the analyze stream and prevent the sample from migrating down the separation column. To inject a small aliquot of sample, the potentials at the buffer and analyze waste reservoir are simply floated for a short period of time (≈100 as) allowing sample to migrate down the separation column as in analyze injection. To break off the injection plug the potentials at the buffer and analyze waste reservoir are reapplied. A shortfall of this method is that the composition of the injected plug has analyze bias whereby the faster migrating compounds are introduced preferentially into the separation column over slower migrating compounds.

The use of micromachined post-column reactors can improve the power of post-separation reactions as an analytical tool by minimizing the volume of the extra-column plumbing especially between the separation and reagent columns. this microchip design was fabricated with a modest lengths for the separation (7 mm) and reaction columns (10.8 mm) which were more than sufficient for this demonstration. Longer separation columns can be manufactured on a similar size microchip using a serpentine geometry [15] to perform more difficult separations. To decrease post-mixing tee band distortions, the ratio of the channel dimensions between the separation column and reaction column should be minimized so that the electric field strength in the separation channel is large, i.e. narrow channel, and in the reaction channel is small, i.e. wide channel.

While advantageous embodiments have been chosen to illustrate the invention, it will be understood by those skilled in the art that various changes and modifications can be made therein without departing from the scope of the invention as defined in the appended claims.

What is claimed is:

1. A method of sample injection, comprising:
providing a microchip having first, second, third and fourth channel segments, the first, second, third and fourth channel segments communicating at an intersection;
moving a first material from a first channel segment into the intersection; and
subsequently moving the first material in the intersection into the second channel segment and simultaneously moving the first material in the first channel segment away from the intersection.

2. The method of claim 1, wherein the step of moving the first material into the intersection comprises moving the first material through the intersection into the third channel segment.

3. The method of claim 2, wherein the step of subsequently moving the portion of first material into the second channel segment comprises simultaneously moving the first material in the first channel segment and the first material in the third channel segment away from the intersection.

4. The method of claim 2, wherein the step of moving the first material through the intersection and into the third channel segment comprises moving a second material from the at least one of the second and fourth channel segments into the intersection.

5. The method of claim 2, wherein the step of moving the first material through the intersection and into the third channel segment comprises moving at least a second material from each of the second and fourth channel segments into the intersection.

6. The method of claim 5, wherein the step of moving the at least second material from the second and fourth channel segments into the intersection further comprises moving the second material through the intersection into the third channel segment.

7. The method of claim 1, wherein the step of moving the first material from the first channel segment into the intersection comprises applying an electric field between the first channel segment and the third channel segment, through the intersection.

8. The method of claim 7, wherein the step of moving the at least first material in the first channel segment away from the intersection comprises applying an electric field between the third channel segment and the first channel segment through the intersection.

9. The method of claim 1, wherein the second channel segment communicates with the intersection between the first channel segment and the third channel segment and the fourth channel segment communicates with the intersection between the third channel segment and the first channel segment.

10. The method of claim 9, wherein the first channel segment is directly across the intersection from the third channel segment.

11. The method of claim 1, wherein the intersection comprises a cross intersection.

12. The method of claim 1, wherein the first material comprises nucleic acids.

13. The method of claim 1, further comprising detecting at least a portion of the first material in the second channel segment.

14. The method of claim 13, wherein the first material comprises a detectable label associated therewith.

15. The method of claim 14, wherein the detectable label comprises a fluorescent label.

16. The method of claim 14, wherein the detecting step comprises exciting the fluorescent label, and detecting emitted fluorescence in the second channel segment.

17. The method of claim 16, wherein the fluorescent label is excited in the second channel segment using a laser.

18. The method of claim 16, wherein the fluorescent label is excited in the second channel segment using a laser diode.

19. The method of claim 16, wherein the fluorescent label is excited in the second channel segment using a LED.

20. A method of sample injection, comprising:
providing a substrate having first, second, third and fourth channel segments, the first, second, third and fourth channel segments communicating at a confluence region;
moving a first material from a first channel segment into the confluence region; and
subsequently moving the first material in the confluence region into the second channel segment and simultaneously moving the first material in the first channel segment away from the confluence region.

21. The method of claim 20, wherein the confluence region comprises a microscale channel segment, the first, second, third and fourth channel segments being in fluid communication with the microscale channel segment, and wherein the moving step comprises moving the first material from the first channel segment into the microscale channel segment.

22. The method of claim 21, wherein the step of moving the first material from the first channel segment into the confluence region comprises applying an electric field between the first channel segment and the third channel segment, through the confluence region.

23. The method of claim 22, wherein the step of moving the at least first material in the first channel segment away from the confluence region comprises applying an electric field between the third channel segment and the first channel segment through the confluence region.

24. The method of claim 21, wherein the second channel segment communicates with the confluence region between the first channel segment and the third channel segment and the fourth channel segment communicates with the confluence region between the third channel segment and the first channel segment.

25. The method of claim 21, wherein the confluence region comprises a channel intersection.

26. The method of claim 25, wherein the first channel segment is directly across the intersection from the third channel segment.

27. The method of claim 21, wherein the first material comprises nucleic acids.

28. The method of claim 21, further comprising detecting at least a portion of the first material in the second channel segment.

29. The method of claim 28, wherein the first material comprises a detectable label associated therewith.

30. The method of claim 29, wherein the detectable label comprises a fluorescent label.

31. The method of claim 30, wherein the detecting step comprises exciting the fluorescent label, and detecting emitted fluorescence in the second channel segment.

32. The method of claim 31, wherein the fluorescent label is excited in the second channel segment using a laser.

33. The method of claim 31, wherein the fluorescent label is excited in the second channel segment using a laser diode.

34. The method of claim 31, wherein the fluorescent label is excited in the second channel segment using a LED.

35. The method of claim 20, wherein in the providing step, the confluence region comprises a microscale channel segment, the first, second, third and fourth channel segments being in fluid communication with the microscale channel segment, and wherein the moving step comprises moving the first material from the first channel segment into the microscale channel segment and into the third channel segment.

36. The method of claim 35, wherein the first channel segment is in fluid communication with the microscale channel region at a point across from a point at which the third channel segment is in fluid communication with the microscale channel segment.

37. The method of claim 20, wherein the step of moving the first material into the confluence region comprises moving the first material through the confluence region into the third channel segment.

38. The method of claim 37, wherein the step of subsequently moving the portion of first material into the second channel segment comprises simultaneously moving the first material in the first channel segment and the first material in the third channel segment away from the confluence region.

39. The method of claim 37, wherein the step of moving the first material through the confluence region and into the third channel segment comprises moving a second material from the at least one of the second and fourth channel segments into the confluence region.

40. The method of claim 37, wherein the step of moving the first material through the confluence region and into the third channel segment comprises moving at least a second material from each of the second and fourth channel segments into the confluence region.

41. The method of claim 40, wherein the step of moving the at least second material from the second and fourth channel segments into the confluence region further comprises moving the second material through the confluence region into the third channel segment.

42. A method of sample injection, comprising:
providing a substrate having first, second, third and fourth channel segments, the first, second, third and fourth channel segments communicating at a first microscale channel region;
moving a first material from the first channel segment into the first microscale channel region; and
injecting the first material in the first microscale channel region into the second channel segment while simultaneously moving the first material in the first channel segment away from the first microscale channel region.

43. The method of claim 42, wherein the first material is electrokinetically moved from the first channel segment into the first microscale channel region.

44. The method of claim 42, wherein the first material in the first microscale channel region is electrokinetically injected into the second channel segment and the first material in the first channel segment is electrokinetically moved away from the first microscale channel region.

45. The method of claim 42, wherein the step of moving the first material into the first microscale channel region comprises moving the first material through the first microscale channel region into the third channel segment.

46. The method of claim 42, wherein the step of subsequently moving the portion of first material into the second channel segment comprises simultaneously moving the first material in the first channel segment and the first material in the third channel segment away from the first microscale channel region.

47. The method of claim 42, wherein the step of moving the first material through the first microscale channel region and into the third channel segment comprises moving a second material from the at least one of the second and fourth channel segments into the first microscale channel region.

48. The method of claim 42, wherein the step of moving the first material through the first microscale channel region and into the third channel segment comprises moving at least a second material from each of the second and fourth channel segments into the first microscale channel region.

49. The method of claim 48, wherein the step of moving the at least second material from the second and fourth channel segments into the first microscale channel region further comprises moving the second material through the first microscale channel region into the third channel segment.

50. The method of claim 42, wherein the second channel segment communicates with the first microscale channel region between the first channel segment and the third channel segment and the fourth channel segment communicates with the first microscale channel region between the third channel segment and the first channel segment.

51. The method of claim 50, wherein the first channel segment is directly across the first microscale channel region from the third channel segment.

52. The method of claim 42, wherein the first material comprises nucleic acids.

53. The method of claim 42, further comprising detecting at least a portion of the first material in the second channel segment.

54. The method of claim 53, wherein the first material comprises a detectable label associated therewith.

55. The method of claim 54, wherein the detectable label comprises a fluorescent label.

56. The method of claim 55, wherein the detecting step comprises exciting the fluorescent label, and detecting emitted fluorescence in the second channel segment.

57. The method of claim 56, wherein the fluorescent label is excited in the second channel segment using a laser.

58. The method of claim 56, wherein the fluorescent label is excited in the second channel segment using a laser diode.

59. The method of claim 56, wherein the fluorescent label is excited in the second channel segment using a LED.

* * * * *